(12) United States Patent
Murthy et al.

(10) Patent No.: US 9,927,334 B2
(45) Date of Patent: Mar. 27, 2018

(54) METHODS, COMPOSITIONS AND DEVICES EMPLOYING ALGINIC ACID HYDROGELS FOR HIGHLY SPECIFIC CAPTURE AND RELEASE OF BIOLOGICAL MATERIALS

(75) Inventors: Shashi K. Murthy, Newton, MA (US); Adam Hatch, Cambridge, MA (US); George Hansmann, Boston, MA (US)

(73) Assignee: Northeastern University, Boston, MA (US)

( * ) Notice: Subject to any disclaimer, the term of this patent is extended or adjusted under 35 U.S.C. 154(b) by 1026 days.

(21) Appl. No.: 13/982,680

(22) PCT Filed: Feb. 3, 2012

(86) PCT No.: PCT/US2012/023859
§ 371 (c)(1),
(2), (4) Date: Nov. 13, 2013

(87) PCT Pub. No.: WO2012/106658
PCT Pub. Date: Aug. 9, 2012

(65) Prior Publication Data
US 2014/0057280 A1    Feb. 27, 2014

Related U.S. Application Data

(60) Provisional application No. 61/439,166, filed on Feb. 3, 2011.

(51) Int. Cl.
*B01L 3/00* (2006.01)
*B01F 5/06* (2006.01)
(Continued)

(52) U.S. Cl.
CPC ............... *G01N 1/34* (2013.01); *B01F 5/061* (2013.01); *B01F 13/0059* (2013.01);
(Continued)

(58) Field of Classification Search
CPC .................. B01F 5/061; B01F 13/0059; B01F 2005/0623; B01F 2005/0636;
(Continued)

(56) References Cited

U.S. PATENT DOCUMENTS 6,642,363 B1 * 11/2003 Mooney ................. A61K 35/34
                                                    536/124
7,204,139 B2 * 4/2007 Takayama ............. B01F 5/0646
                                                    73/204.26

(Continued)

FOREIGN PATENT DOCUMENTS

EP         2177236 A1    4/2010
WO    WO-9812228 A1    3/1998

(Continued)

OTHER PUBLICATIONS

International Search Report and Written Opinion dated May 25, 2012 for International Application No. PCT/US2012/023859 (9 pgs.).

(Continued)

*Primary Examiner* — Scott Long
*Assistant Examiner* — Gary E Hollinden
(74) *Attorney, Agent, or Firm* — Posternak Blankstein & Lund LLP

(57) ABSTRACT

Disclosed herein are hydrogel compositions and methods of making hydrogel compositions. Furthermore, methods of specifically capturing and releasing biological materials from a sample using the disclosed hydrogel compositions are disclosed, including methods of utilizing the compositions in microfluidic devices.

13 Claims, 14 Drawing Sheets

Gel types II-IV; all reagents combined together

Gel type V: two step mixing protocol with PEG, antibody, EDC, and sulfo NHS in first step

(51) Int. Cl.
  G01N 33/569    (2006.01)
  G01N 1/34      (2006.01)
  G01N 33/543    (2006.01)
  G01N 33/548    (2006.01)
  B01F 13/00     (2006.01)

(52) U.S. Cl.
  CPC ..... *G01N 33/548* (2013.01); *G01N 33/54386* (2013.01); *G01N 33/56966* (2013.01); *B01F 2005/0623* (2013.01); *B01F 2005/0636* (2013.01); *B01L 3/502761* (2013.01); *B01L 2200/0636* (2013.01); *B01L 2200/0652* (2013.01); *B01L 2300/069* (2013.01); *B01L 2300/0867* (2013.01); *B01L 2400/0478* (2013.01)

(58) Field of Classification Search
  CPC ........... G01N 33/54386; G01N 33/548; G01N 33/56966; G01N 1/34; B01L 3/502761; B01L 2200/0636; B01L 2200/0652; B01L 2300/069; B01L 2300/0867; B01L 2400/0478
  See application file for complete search history.

(56) References Cited

U.S. PATENT DOCUMENTS

| | | | |
|---|---|---|---|
| 2006/0094060 A1* | 5/2006 | Jarhede | B82Y 30/00 435/7.1 |
| 2006/0121012 A1 | 6/2006 | Kutryk et al. | |
| 2007/0259424 A1 | 11/2007 | Toner et al. | |
| 2010/0144902 A1* | 6/2010 | Shu | C08G 75/04 514/774 |
| 2010/0261270 A1* | 10/2010 | Peeters | C12N 5/0068 435/347 |
| 2014/0154703 A1* | 6/2014 | Skelley | B01L 3/502761 435/7.23 |

FOREIGN PATENT DOCUMENTS

| | | |
|---|---|---|
| WO | WO-0340235 A1 | 5/2003 |
| WO | WO-2009074932 A1 | 6/2009 |
| WO | WO-2010124227 A2 | 10/2010 |

OTHER PUBLICATIONS

Yamaguchi, et al., "Polysaccharide-Poly(ethylene glycol) Star Copolymer as a Scaffold for the Production of Bioactive Hydrogels," Biomacromolecules, 2005, 6(4), p. 1921-1930.

Extended European Search Report issued by the European Patent Office for European Application No. 12742728.4 dated Oct. 31, 2014 (11 pgs.).

Hatch, et al., "Engineered Alginate Hydrogels for Effective Microfluidic Capture and Release of Endothelial Progenitor Cells from Whole Blood," Langmuir, vol. 27, No. 7, pp. 4257-4264 (Apr. 5, 2011).

Mahou, et al., "Novel Alginate-Poly(ethylene glycol) Hydrogel for Immobilization and Delivery: Synthesis and Physical Properties Assessment," XVIIth International Conference on Bioencapsulation, Groningen, Netherlands, Sep. 24-26, 2009 (2 pgs.).

Plouffe, et al., "Controlled Capture and Release of Cardiac Fibroblasts Using Peptide-Functionalized Alginate Gels in Microfluidic Channels," Lab on a Chip, vol. 9, No. 11, pp. 1507-1510 (Jan. 1, 2009).

* cited by examiner

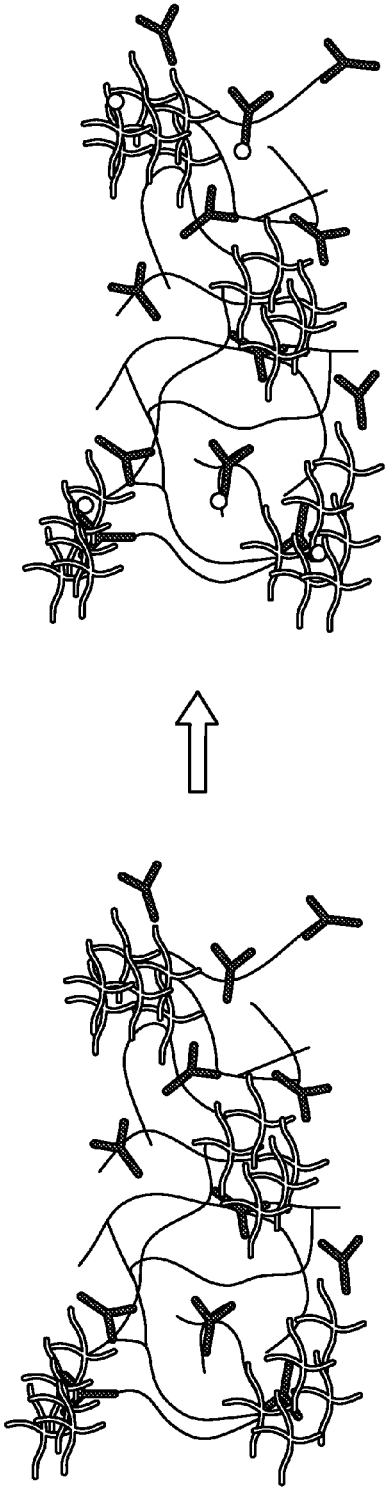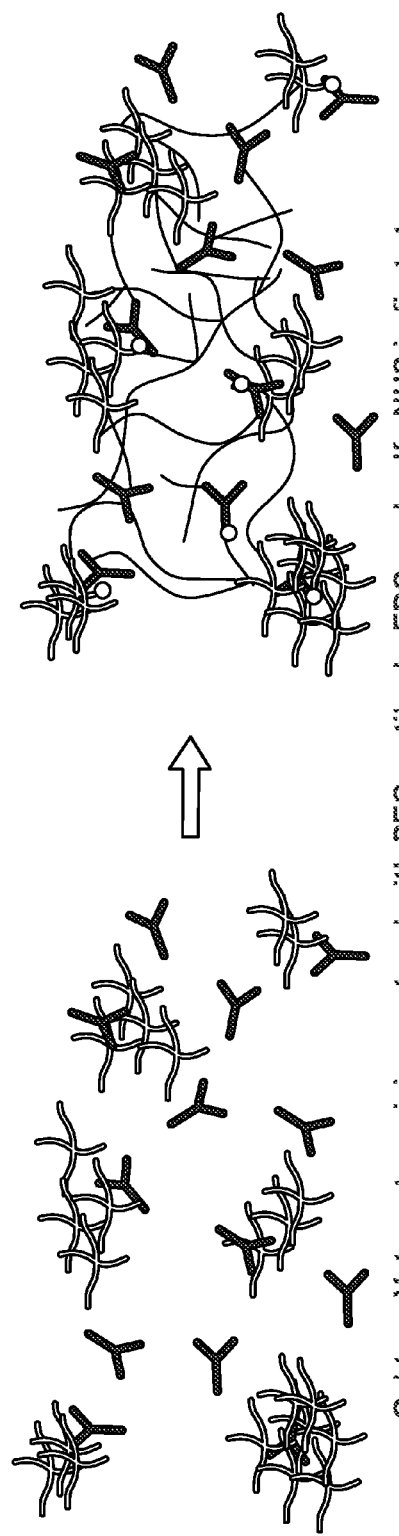
FIG. 4a  Gel types II-IV: all reagents combined together
FIG. 4b  Gel type V: two step mixing protocol with PEG, antibody, EDC, and sulfo NHS in first step

| Sample | Injection Rate | Percent BSA (w/v) | pH | Alginate Formulation Step I (Mix/Incubation) | Alginate Formulation Step II (Mix/Incubation) |
|---|---|---|---|---|---|
| I-Injected | - | - | - | - | - |
| II | 3μL/min | 0.1% | 6.0 | 29/60 | 29/60 |
| III | 3μL/min | 0.1% | 6.0 | 29/0 | 60/0 |
| IV | 5μL/min | 0.1% | 6.0 | 29/0 | 60/0 |
| V | 5μL/min | 1.0% | 6.0 | 29/0 | 60/0 |
| VI | 3μL/min | 0.1% | 4.7 | 29/0 | 60/0 |

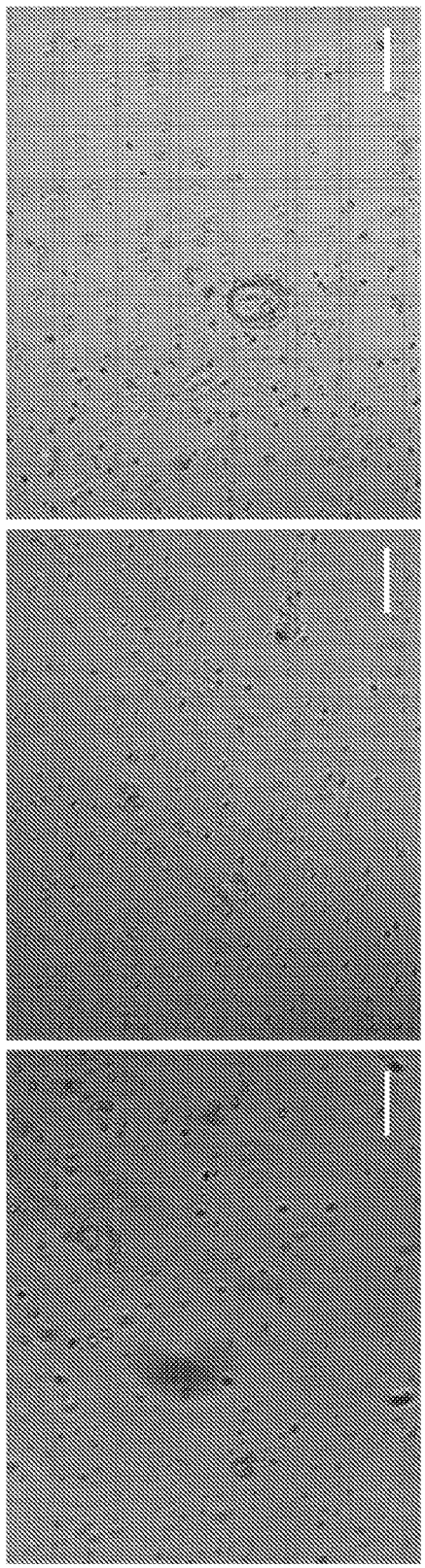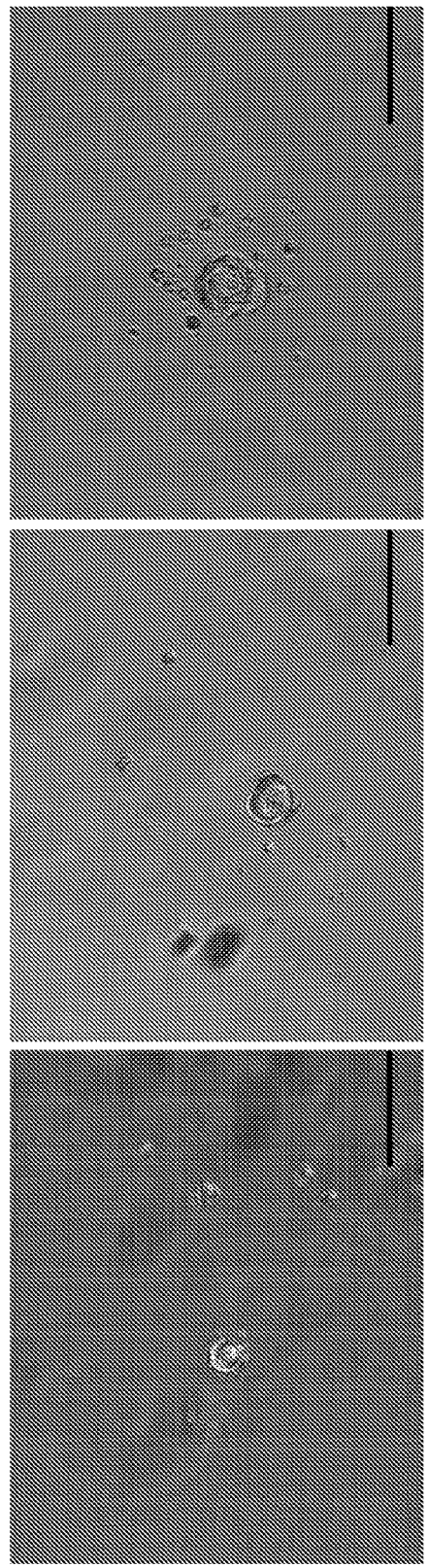
FIG. 7c  FIG. 7f
FIG. 7b  FIG. 7e
FIG. 7a  FIG. 7d

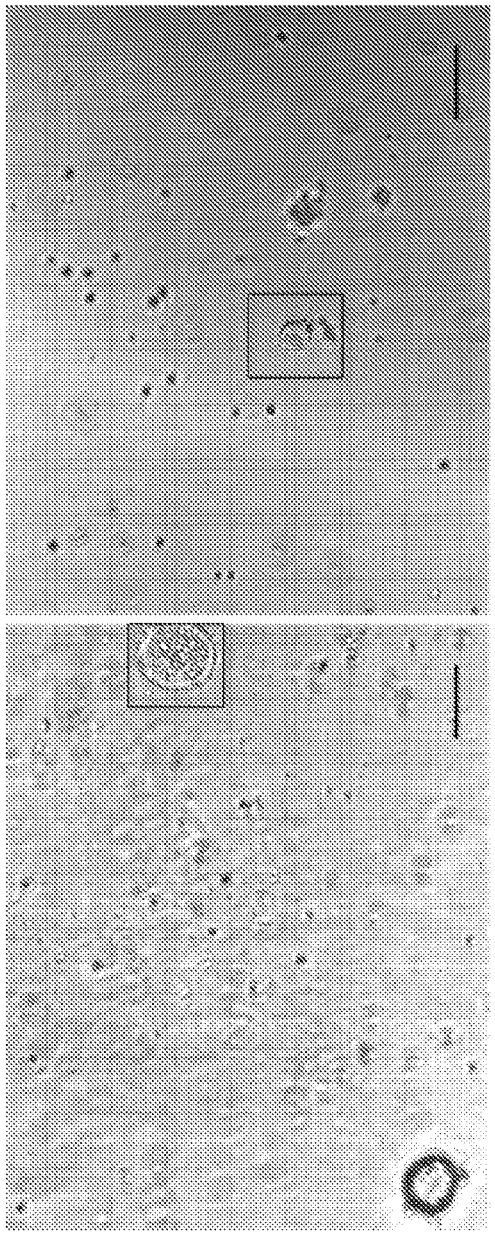
FIG. 8a
FIG. 8b
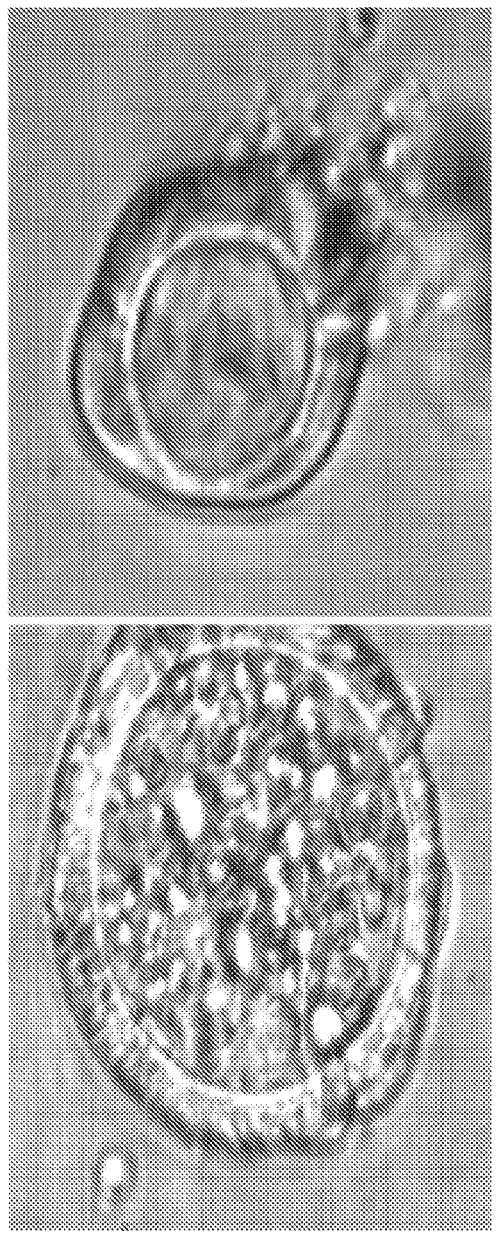
FIG. 8c
FIG. 8d

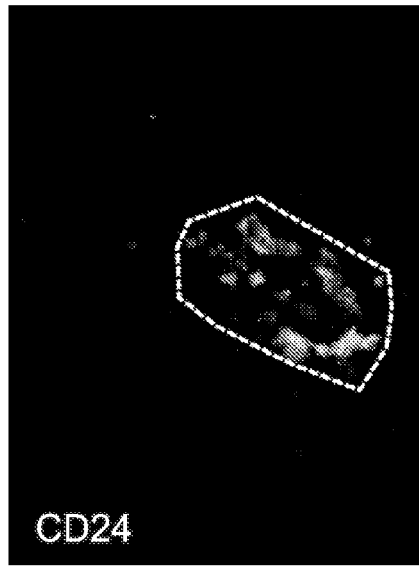
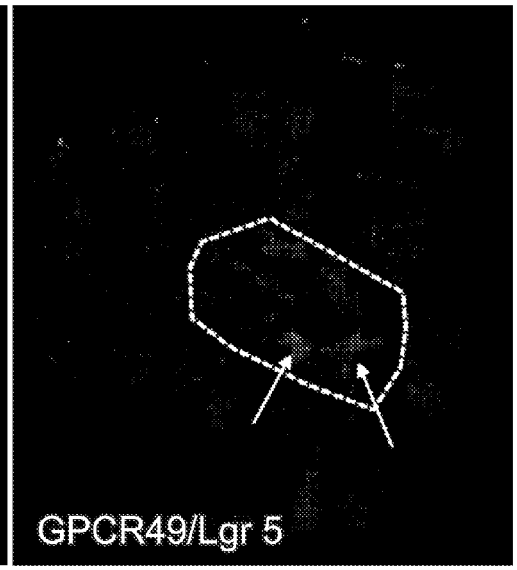
FIG. 10a  FIG. 10b
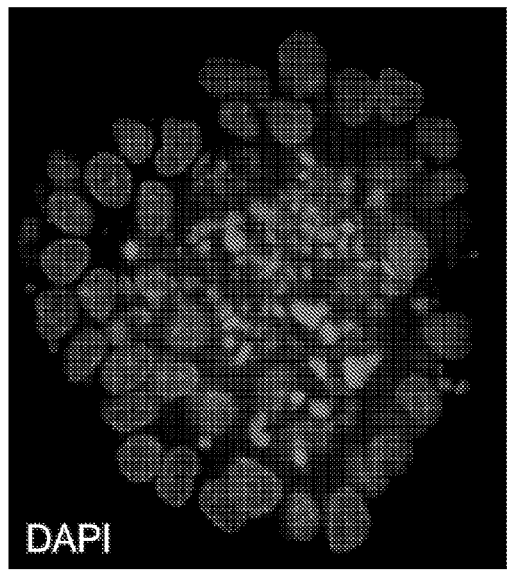
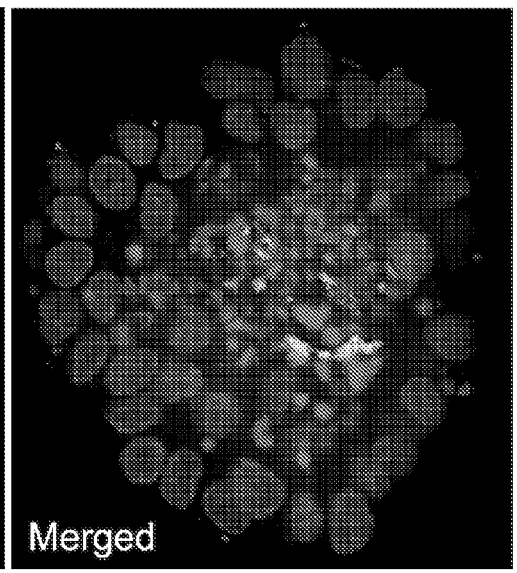
FIG. 10c  FIG. 10d

METHODS, COMPOSITIONS AND DEVICES EMPLOYING ALGINIC ACID HYDROGELS FOR HIGHLY SPECIFIC CAPTURE AND RELEASE OF BIOLOGICAL MATERIALS

CROSS REFERENCE TO RELATED APPLICATIONS

This application is a National Stage Entry of PCT International Application No. PCT/US2012/23859, filed on Feb. 3, 2012, which claims priority to U.S. Provisional Application No. 61/439,166, filed on Feb. 3, 2011, the contents of which are hereby incorporated by reference in their entirety.

FEDERALLY SPONSORED RESEARCH OR DEVELOPMENT

This invention was sponsored through grants from the National Institutes of Health and the National Science Foundation under grants R01-EB009327 and CBET 0932195, respectively. Thus, the U.S. government has certain rights in this application.

FIELD OF THE INVENTION

The invention is generally directed to medicine and engineering. More specifically, the field is directed to isolation of biological materials, such as cells, for tissue engineering and regenerative medicine.

BACKGROUND

Cellular isolation techniques are an essential component in studying specific populations, allowing for growth, genomic, and proteomic investigations. The detachment of cells adhered to any surface requires the application of a force that is greater in magnitude to that of adhesion. Fluid shear forces have been shown to be a simple method for cell detachment. Although this is a local and simple method of cell release, excessive exposure to fluid shear results in cell damage and reduction in viability. An alternative approach is to cleave the protein ligand that is bound to the capture surface using enzymes, such as trypsin. However, enzymatic exposure can cause morphological changes due to a disruption of the cell membrane and glycocalyx, leading to losses in cellular activity. Furthermore, enzymatic digestion has been shown to directly affect both the behavior and chemical makeup of the cells themselves.

Current techniques, such as fluorescent activated cell sorting (FACS) and magnetic activated cell sorting (MACS), in cell isolation have disadvantages in fields such as tissue engineering. Conventional method of cell isolation, FACS, presents limited throughput which can be detrimental to the cell viability. The FACs method is limited in its ability to multiplex, which leads to sample processing time to decrease substantially.

These limitations illustrate the need to establish a general technique to capture and release biological materials, such as cells, in micro-scale devices without extensive physical or chemical perturbations to the cell environment. There remains a need for surfaces and gels that have high specificity for particular cells and that allow the release of captured cells without altering the behavior and makeup of the cells.

SUMMARY

The present disclosure relates to compositions and methods for the capture and release of biological materials, such as cells. In some embodiments, the capture is highly specific.

In one aspect, the disclosed hydrogel compositions comprise a plurality of alginic acid molecules and a plurality of branched polymer molecules. The plurality of alginic acid molecules is conjugated to or blended with the branched polymer molecule or one or more binding agents to form a hydrogel, and each of the branched polymer molecules comprises a plurality of groups. Furthermore, in aspects disclosed herein, at least one group of each branched polymer molecule is conjugated to an alginic acid molecule and at least one other group of each branched polymer molecule is conjugated to one or more binding agents.

In some embodiments, the branched polymer molecule is a polyethylene glycol molecule. In some embodiments, the polyethylene glycol molecule is a four-arm molecule.

In some embodiments, the one or more binding agents is an antibody, antibody fragment, peptidomimetic compound, peptide, small molecule, or nucleic acid.

In some embodiments, the antibody is selected from the group consisting of antibodies against GPR49, LGR5, CD24, FLK1, CD45, CD31, CD34, and sca-1.

In one aspect, the disclosed methods capturing and releasing target biological materials from a sample comprise providing a microfluidic device comprising one or more chambers for receiving fluids, wherein at least one of the one or more chambers comprises a surface coated with a hydrogel composition. The hydrogel composition comprises a plurality of alginic acid molecules and a plurality of branched polymer molecules in which the plurality of alginic acid molecules is conjugated to or blended with the branched polymer molecule or one or more binding agents to form a hydrogel. In certain aspects disclosed herein, each of the branched polymer molecule comprises a plurality of groups, at least one group of each branched polymer molecule is conjugated to an alginic acid molecule and at least one other group of each branched polymer molecule is conjugated to one or more binding agents. The methods further comprise introducing a sample comprising target and non-target biological materials into the one or more chambers under conditions effective to bind the target biological materials to the hydrogel composition and releasing the target biological materials using a releasing agent.

In some embodiments, the methods further comprise removing the unbound non-target materials from the sample.

In another aspect, the disclosed methods of capturing and releasing target biological materials from a sample comprise providing a microfluidic device comprising one or more chambers for receiving fluids, wherein at least one of the one or more chambers comprises at least one surface coated with a hydrogel composition. The hydrogel composition comprises a plurality of alginic acid molecules and a plurality of branched polymer molecules in which the plurality of alginic acid molecules is conjugated to the branched polymer molecule or one or more binding agents to form a hydrogel. In certain aspects, each of the branched polymer molecule comprises a plurality of groups, at least one group of each branched polymer molecule is conjugated to an alginic acid molecule and at least one other group of each branched polymer molecule is conjugated to one or more binding agents. Furthermore, the methods comprise introducing a sample comprising target biological materials into a first chamber of the device under conditions effective to bind biological materials to the hydrogel composition and releasing the bound biological materials using a releasing agent. The methods also comprise contacting the releasing agent with a neutralizing agent to neutralize the releasing agent in a second chamber and providing the contents of the second chamber into a third chamber comprising a surface coated with the hydrogel composition, wherein the binding agent in the third chamber is a different binding agent than that used in (a), under conditions effective to bind the target biological materials to the hydrogel composition. In addition, the methods comprise releasing the bound, target biological materials using a releasing agent.

In some embodiments, the methods further comprise adding culture medium to the released biological materials.

In some embodiments, the methods further comprise repeating (d) through (f) using a different binding agent.

In some embodiments, the methods further comprise detecting the target biological materials after release from the hydrogel composition.

In some embodiments, the biological materials used in the disclosed methods are cells, proteins, solutes, or particulates, and wherein the releasing agent is a chelating agent, an enzyme, or a combination thereof.

In some embodiments, the cells are adult stem cells, fetal stem cells, progenitor cells, peripheral hematopoietic stem cells, endothelial progenitor cells, circulating tumor cell, mature circulating endothelial cells, amniotic stem cells, mesenchymal stem cells, adipose-derived stem cells, intestinal stem cells, skin stem cells, neural stem cells, or cancer stem cells.

In some embodiments, the cell is a living cell captured from the sample.

In some embodiments, the chelating agent used in the disclose methods is selected from the group consisting of EDTA, EGTA, and sodium citrate.

In some embodiments, the disclosed methods further comprise maintaining the living cell under conditions effective to culture, detect, analyze, or transform the living cell.

In another aspect, methods of making a hydrogel composition are disclosed. The methods comprise reacting branched polymer molecules with one or more binding agents in a buffer and reacting the branched polymer-binding agent solution with at least one alginic acid molecule to form a functionalized hydrogel. The functionalized hydrogel comprises each of the branched polymer molecules conjugated to one or more binding agents and further conjugated to at least one alginic acid molecule.

In some embodiments, the branched polymer molecule is a polyethylene glycol molecule. In some embodiments, the polyethylene glycol molecule is a four-arm molecule.

In some embodiments, the one or more binding agents is an antibody, antibody fragment, peptidomimetic compound, peptide, small molecule, or a nucleic acid.

In some embodiments, the antibody is selected from the group consisting of antibodies against GPR49, LGR5, CD24, FLK1, CD45, CD31, CD34, and sca-1.

In another aspect, the disclosed microfluidic device comprises a substrate and one or more chambers for receiving a sample comprising target biological materials. The one or more chambers comprise a surface coated with a hydrogel composition, the hydrogel composition comprising a plurality of alginic acid molecules and a plurality of branched polymer molecules. The plurality of alginic acid molecules is conjugated to or blended with the branched polymer molecule or one or more binding agents to form a hydrogel. In addition, each of the branched polymer molecule comprises a plurality of groups, at least one group of each branched polymer molecule is conjugated to an alginic acid molecule. Also, at least one other group of each branched polymer molecule is conjugated to a binding agent. A mixing chamber is also included for mixing bound target biological materials with a neutralizing agent. Furthermore, in certain aspects, one or more additional surfaces are coated with a hydrogel composition. The hydrogel composition comprises a plurality of alginic acid molecules and a plurality of branched polymer molecules in which the plurality of alginic acid molecules is conjugated to the branched polymer molecule or one or more binding agents to form a hydrogel. Also, each of the branched polymer molecule comprises a plurality of groups, at least one group of each branched polymer molecule is conjugated to an alginic acid molecule. Furthermore, at least one other group of each branched polymer molecule is conjugated to a binding agent that is different from the binding agent in step (i).

In some embodiments, the branched polymer in the disclosed devices is polyethylene glycol molecule. In some embodiments, the polyethylene glycol molecule is a four-arm molecule.

In some embodiments, the one or more binding agents used in the disclosed devices is an antibody, antibody fragment, peptidomimetic compound, peptide, small molecule, or nucleic acid.

In some embodiments, the antibody is selected from the group consisting of antibodies against GPR49, LGR5, CD24, FLK1, CD45, CD31, CD34, and sca-1.

SHORT DESCRIPTION OF THE FIGURES

The following figures are presented for the purpose of illustration only, and are not intended to be limiting:

Figure 4C:
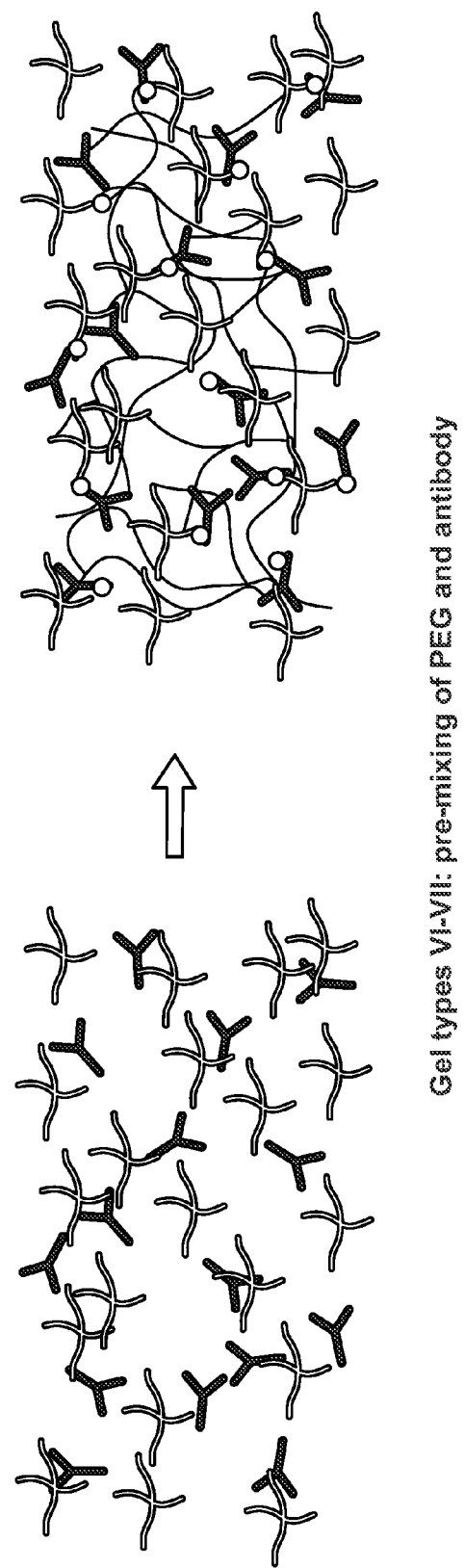

FIGS. 4A-C are graphic representations showing structural differences in different gel types. In FIG. 4A, all reagents (including PEG, antibody, alginic acid) are combined together in gel types II-IV. In FIG. 4B, Gel Type V utilizes a two-step protocol in which the PEG, antibody, EDC, and sulfo-NHS are combined in a single first step. In FIG. 4C, Gel Types VI-VII has pre-mixing of PEG and antibody prior to mixing other components.

Figure 5A:
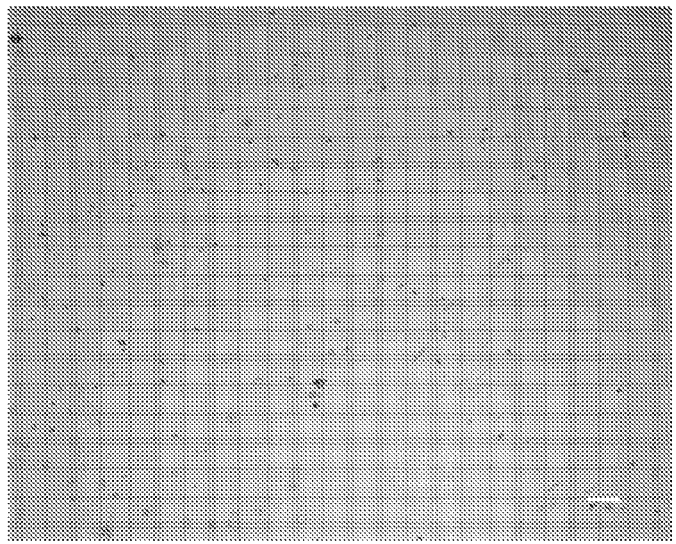
Figure 5B:
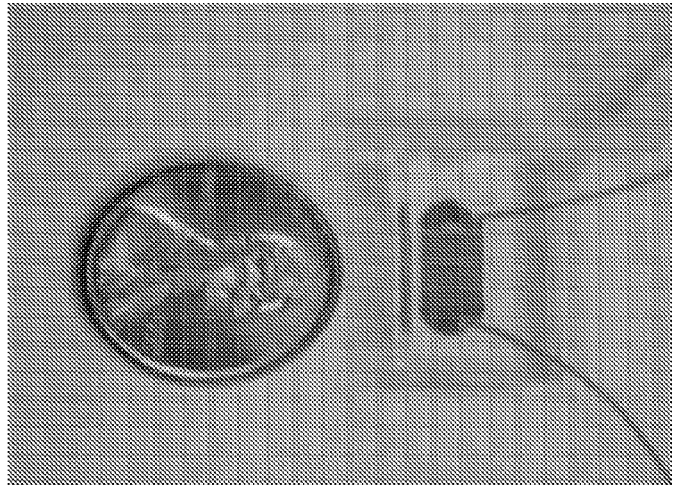
Figure 5C:
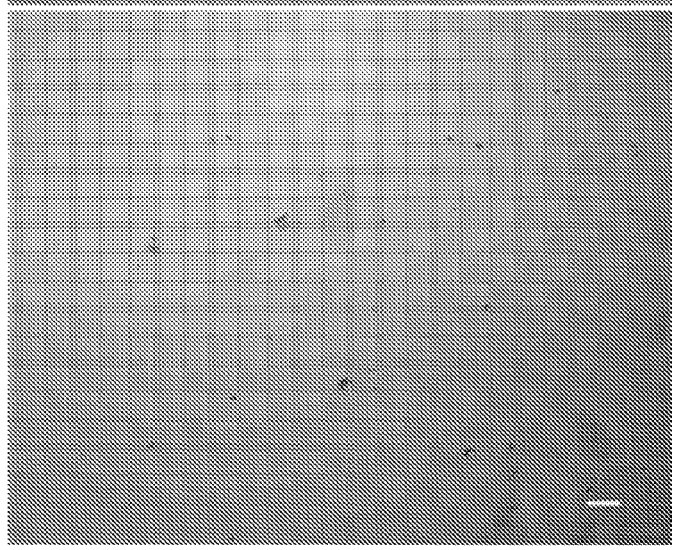

FIGS. 5A-C depict qualitative representations of injected and released suspension pre- and post-microfluidics array. Injected population (depicted in FIG. 5A) was constrained to a concentration of 100,000-200,000 cells/ml due to settling effects within the chip (depicted in FIG. 5B) at respective concentrations. In FIG. 5C, cells were released into 24-well plates, and a noticeable decrease in cellular density was observed. Scale bar represents 100 μm.

Figures 6A, 6B:
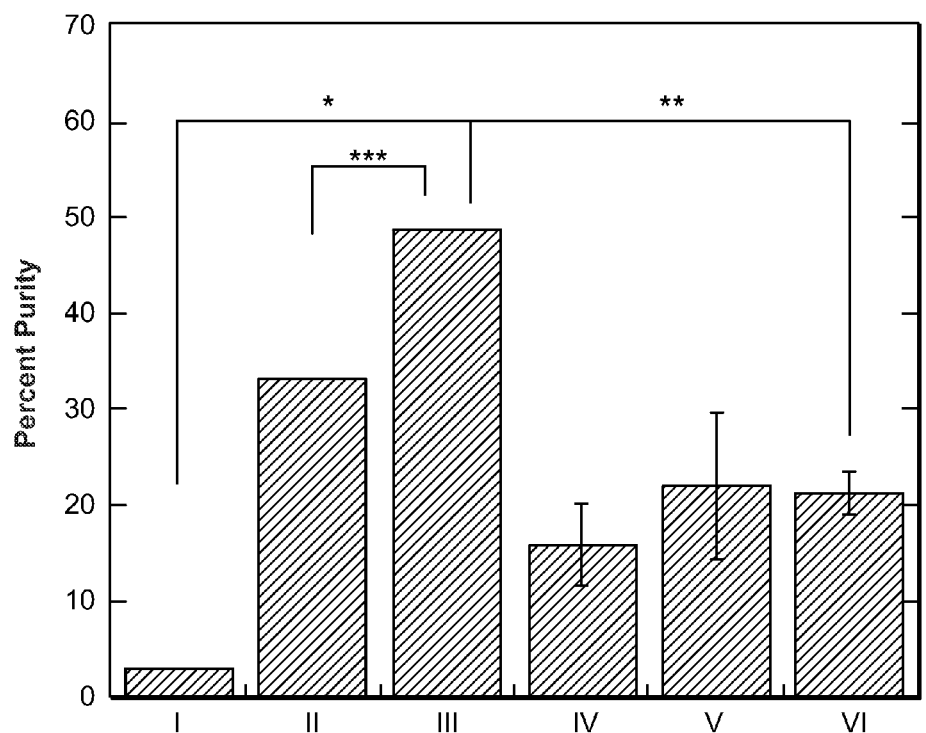

FIGS. 6A-D illustrate that optimization of antibody-functionalized alginate allowed for improved capture efficiency and purity yields. FIG. 6A shows that the samples and formulations were divided into five scenarios, each varying one variable. FIG. 6B compares the purity yield of these scenarios against the injected population. Quantifying the percent purity was preformed via flow cytometry against the injected (FIG. 6C) and the released (FIG. 6D) cells.

FIGS. 7A-F shows age progression of released cells against unenriched population in the absence of Wnt3a protein. Unenriched organoid progression (depicted by FIGS. 7A-C) yielded significant larger cyst-like organoids surrounded by extraneous populations. FIGS. 7D-F depict the 4-day progression of enriched organoid derived from single cell suspension. FIG. 7D depicts the expansion of single cell at day 2, FIG. 7E depicts induced hyperplasia at day 3, and FIG. 7F depicts small lumen formation noticed with surrounding secreted apoptotic cells, at day 4.

FIGS. 8A-D depict enriched and unenriched organoid in the presence of Lgr5 basal media constituents and Wnt3a. FIG. 8A shows that the unenriched population did not have an any increase in plate efficiency in the presence of Wnt3a. FIG. 8C shows that the majority of organoids formed in the injected culture expressed a cyst-like structure harboring apoptotic cells. FIG. 8B shows that the enriched population did have an increase in plating efficiency leading to more single derived organoids proliferating. FIG. 8D shows that enriched cells exhibited similar morphology to the wnt3a absence study (d) at analogous time points.

Figures 9A, 9B:
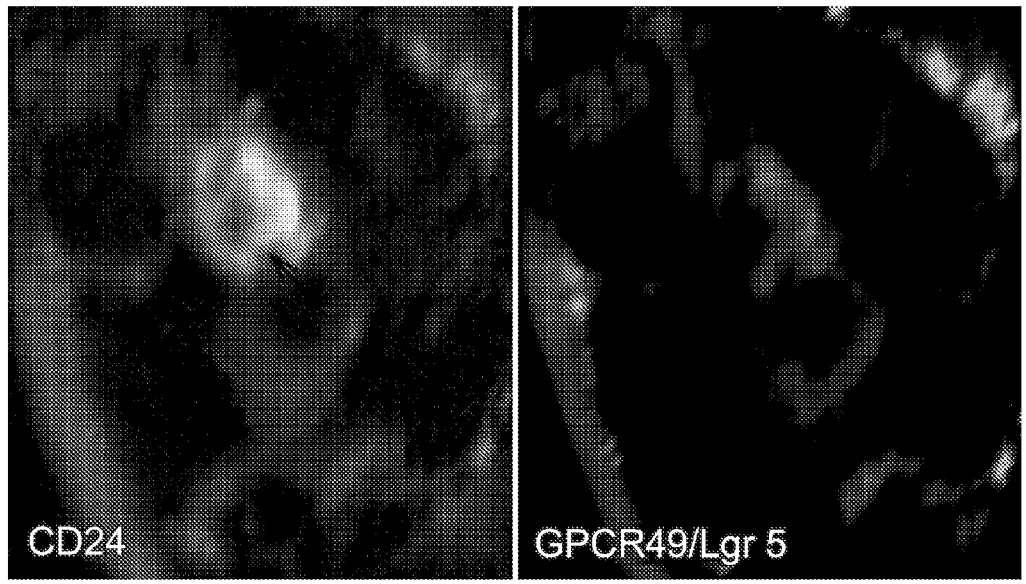
Figures 9C, 9D:
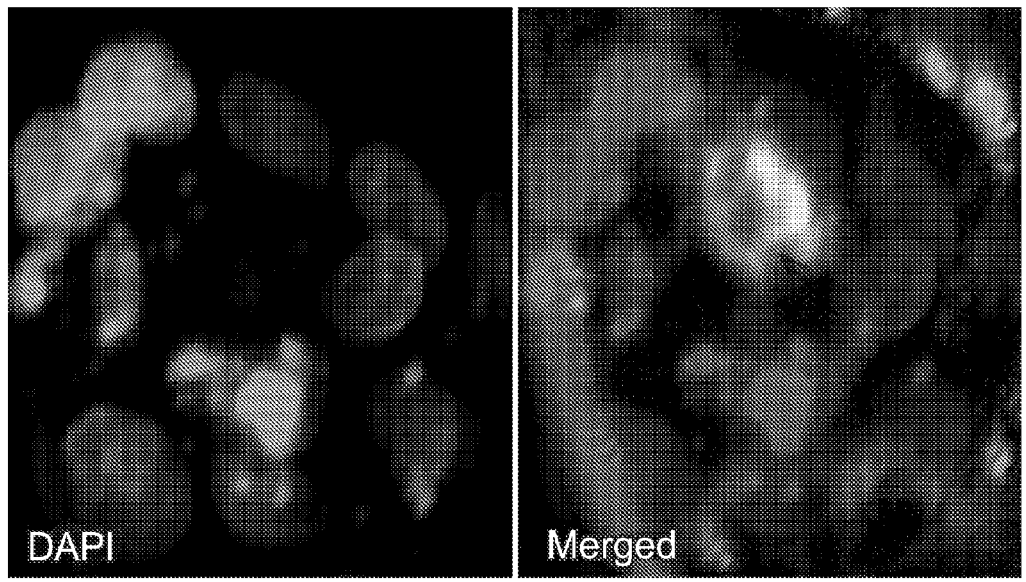

FIGS. 9A-D shows confocal compressed images illustrating the enriched organoid after the disclosed microfluidic isolation technique was used. FIG. 9C depicts lumen formed indicative of the hollow nature in the spherical organoid. FIG. 9A depicts apical localization of CD24, which indicates significant Sox9 expression exhibiting quiescence. FIG. 9B depicts that the isolation capture antibody, GPR49/Lgr5 (b), was prevalent within the central domain, but expression was lower in comparison to CD24.

FIGS. 10A-D represent unenriched organoid confocal images compressed in the z-plane. Organoid was extracted from matrigel after 4 days in culture. Apoptotic cells are notable within the central lumen (FIG. 10C), while the morphology of the organoid is spherical and planar. CD24 expression (FIG. 10A) is apical localized in the central domain and in varying levels of intensity. GPCR49/Lgr5 is present at lower intensity in locations where CD24 is expressed, arrows indicating. The notable presence of GPCR49/Lgr5 expression was trumped by CD24 overlay (FIG. 10D).

FIG. 11A-D represent the sequence of devices for one embodiment of the adhesion-based microfluidic separation of cells against multiple surface markers. Following capture and release from the device (FIG. 11A), cells expressing marker 1 enter a device (FIG. 11B) where a calcium chloride solution is co-injected to neutralize the ethylene diamine tetraacetic acid (EDTA) present in the cell suspension. Another portion of the device (FIG. 11C) mixes the calcium chloride solution and cell suspension. Finally, in FIG. 11D, the chamber captures cells against marker 2, which can then be eluted out using an injection of EDTA solution.

Figure 12:
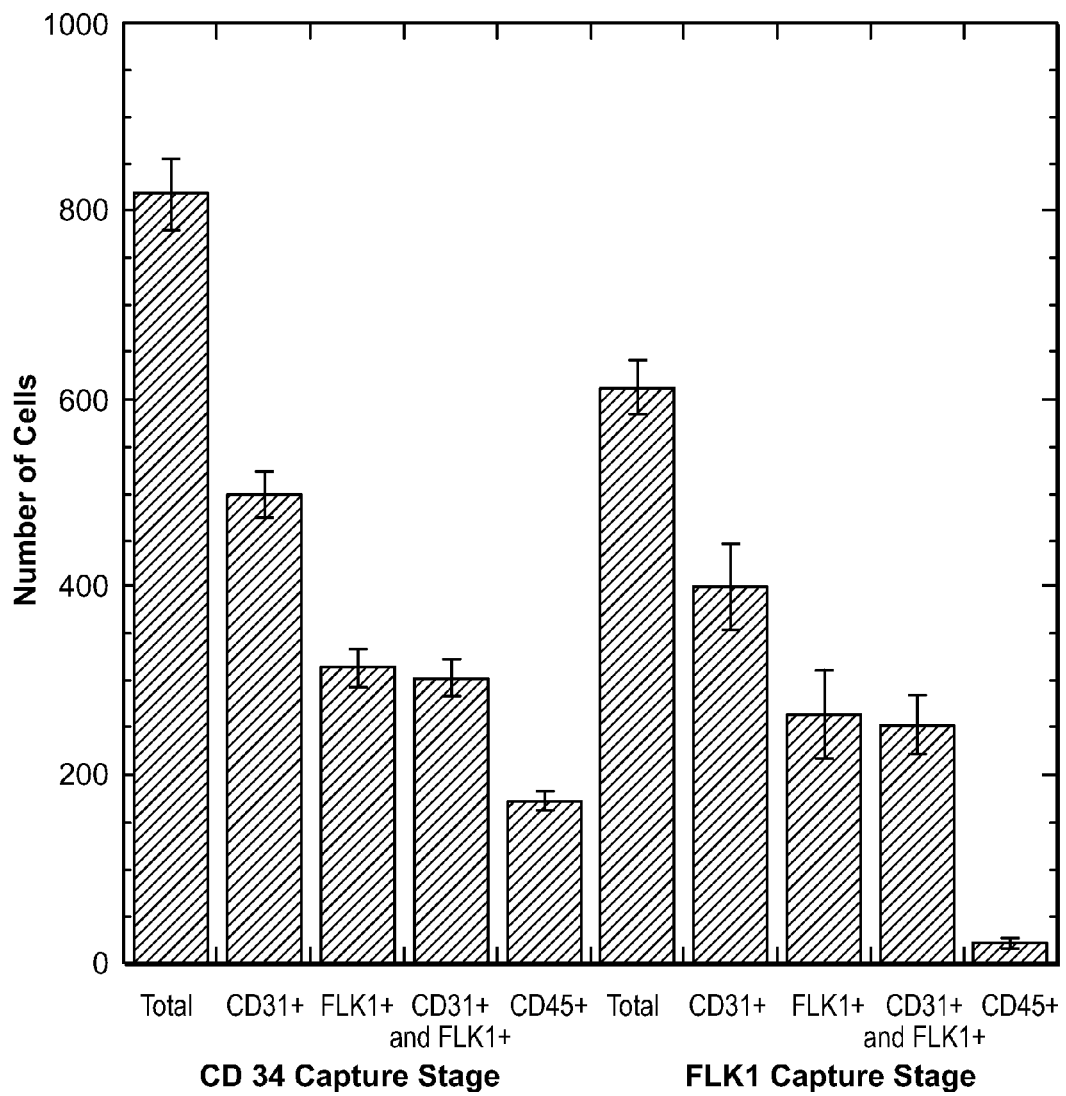

FIG. 12 represents the performance of the multistage capture-release device system in dual-marker separation.

DETAILED DESCRIPTION

The present disclosure relates to compositions and methods for highly specific capture and release of biological materials, such as cells. Hydrogel compositions comprising a plurality of alginic acid molecules conjugated to or blended with branched polymer molecules or one or more binding agents to form a hydrogel are disclosed.

In some embodiments, the disclosed methods and compositions provide surface coatings for the selective capture of a target cell type from a heterogeneous suspension with the additional capability to release captured cells nondestructively. The formulations and techniques disclosed herein allow for altered chemical compositions of alginate hydrogels, which have the ability to bind and release cells but which are prone to significant non-specific cell adhesion, with branched polymers such as poly(ethylene glycol) (PEG) or branched polymers with chemical functional groups known to suppress cell and protein adhesion, including but not limited to fluorocarbons and silicones. The incorporation of the branched polymer into the hydrogel structure is carried out in a way that also enables the functionalization of the alginate pre-polymer with a binding agent (e.g., an antibody, antibody fragment, peptidomimetic compound, peptide, small molecule, or nucleic acid) to provide specificity of capture.

In some embodiments, the synthesis technique is designed for in situ assembly of the hydrogel within confined structures, such as microfluidic channels. The assembly techniques disclosed herein enables coating of channels made from any material, without a requirement for a particular type of material. Flow cytometric analyses of cells captured and detached using this approach from whole blood have indicated that the process is chemically and biologically nondestructive; specifically, there is no or little change in cell viability or phenotypic identity. Furthermore, the inclusion of the branched polymer, such as PEG, within the hydrogel structure overcomes many of the problems associated with known hydrogel capture systems.

The literature describes the design of surface coatings that can facilitate cell detachment when an external stimulus is applied, such as an electrical potential or a small temperature change. An example of the former is a surface coating that consists of ligands bound to the surface via an electroactive chemical functional group. The electroactive quinione ester undergoes a chemical change to lactone upon applying an electrical potential. This approach requires electrode incorporation into the capture device and careful optimization of release parameters. The use of a thermally-responsive polymer, such as poly(N-isopropylacrylamide), which is hydrophobic at 37° C. and hydrophilic at 20° C., is another recently-described approach. The hydrophobic surface is adhesive to cells and its transformation results in nearly-complete cell release.

The shortcomings of such method are the lack of adhesion specificity in a low flow regime and potential adverse effects of lowering the temperature below the physiological temperature of 37° C. Alginate hydrogels have been employed for cell capture and release in microfluidic systems, but without chemical modification with non-adhesive molecules, these hydrogels are extremely prone to non-specific cell and protein adhesion and do not have high efficiencies of cell release.

Advantages of the instant disclosure are that it allows for the selective capture through receptor-ligand interactions. Furthermore, the disclosed methods and devices allow release of target cells from substrates either in static cell culture or flow-based cell separation. The instant disclosure does not require mechanical, enzymatic, electrical or optical interfaces for cell detachment. The disclosed methods and devices can be used without extensive physical or chemical perturbations to the biological environment. Prior techniques, on the other hand, require an external stimulus or require physical or chemical perturbations that compromise, for example, the cellular environment.

The instant disclosure can be used to selectively capture and release biological materials to isolate, for example, stem and progenitor cell populations. The isolated populations can be used for seeding on engineered scaffolds. Engineered replacement organs, and regenerative medicine generally, require pure populations of rare cells to produce a functional organ.

All publications, patent applications, patents, and other references mentioned herein are incorporated by reference in their entirety. In case of conflict, the present specification, including definitions, will control. In addition, the materials, methods, and examples are illustrative only and not intended to be limiting.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Definitions

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The terms "compound" and "compounds" as used in this disclosure refer to the compounds of this disclosure and any and all possible isomers, stereoisomers, enantiomers, diastereomers, tautomers, pharmaceutically acceptable salts, and solvates thereof.

In general, the compositions of the disclosure can be alternately formulated to comprise, consist of, or consist essentially of, any appropriate components disclosed in this disclosure. The compositions of the disclosure can additionally, or alternatively, be formulated so as to be devoid, or substantially free, of any components, materials, ingredients, adjuvants or species used in the prior art compositions or that are otherwise not necessary to the achievement of the function and/or objectives of the present disclosure.

The articles "a" and "an" are used in this disclosure to refer to one or more than one (i.e., to at least one) of the grammatical object of the article. By way of example, "an element" means one element or more than one element.

The term "or" is used in this disclosure to mean, and is used interchangeably with, the term "and/or," unless indicated otherwise.

The term "about" is used in this disclosure to mean a given numerical value plus or minus 20% of the given numerical value.

A "hydrogel" is a three-dimensional, semi-solid network of one or more molecules in which a relatively large amount of water is present. In some instances, the hydrogel can be a polymer. As used herein, a "polymer" is a structure composed of monomers.

"Monomers" are molecules having one or more groups that can react with each other or other types of monomers to form a polymer. A non-limiting example of a monomer is vinyl chloride, which can give a plastic known as "vinyl." Another non-limiting example of a vinyl monomer is acrylamide which can give a gel known as a polyacrylamide gel.

General

The disclosure provides, in part, compositions comprising alginate hydrogels in which alginic acid is in the presence of divalent cations. Such compositions are capable of easily dissolving in the presence of chelators. In addition, the presently disclosed hydrogels are biocompatible and can be functionalized (i.e., conjugated) with cell-adhesive molecules. The alginate hydrogels can be functionalized with binding agents. As used herein, the term "binding agent" means a molecule that binds to another molecule or complex structure. Binding agents include antibodies, antibody fragments, peptidomimetic compounds, peptides, small molecules, and nucleic acids. Antibodies are selected from the group consisting of antibodies against GPR49, LGR5, CD24, FLK1, CD45, CD31, CD34, sca-1, and various other proteins.

The alginate hydrogels can also include branched polymers, such as polyethylene glycol ("PEG") or branched polymers with chemical functional groups known to suppress cell and protein adhesion, including but not limited to fluorocarbons and silicones. The PEG can conjugated to or blended with (that is, functionalized) binding agents. In addition, the PEG can be conjugated to or blended with alginic acid molecules to form a hydrogel. In certain embodiments, the hydrogels utilize 4-arm PEG molecules with primary amine terminations at the end of each arm. A 4-arm PEG molecule has four attachment points for functionalization with other agents such as alginic acid, binding agents, or linkers. In particular embodiments, one arm of each 4-arm PEG molecule binds to a carboxylic acid group to the alginate hydrogel backbone, leaving up to three primary amine groups for functionalization with a binding agent. The 4-arm arrangement allows for triple the binding agent (e.g., antibody) content of the hydrogel and provides protection against non-specific cell binding relative to non PEG-y-lated alginate hydrogels.

In addition, methods are disclosed for making the hydrogels disclosed herein. Methods of making hydrogel compositions comprise reacting polyethylene glycol molecules with one or more binding agents in a buffer and reacting the polyethylene glycol-binding agent solution with at least one alginic acid molecule to form a functionalized hydrogel, the functionalized hydrogel comprising each of the polyethylene glycol molecules conjugated to one or more binding agents and further conjugated to at least one alginic acid molecule.

The methods described herein ensure that at least one attachment point in a branched polymer, such as a PEG molecule, is available for binding with an alginate gel matrix, leaving at least another attachment point for functionalization with binding agents, such as antibodies. Antibodies include but are not limited to antibodies against GPR49, LGR5, CD24, FLK1, CD45, CD31, CD34, sca-1, and various other proteins. In certain embodiments, the methods involve conjugating alginic acid to a binding agent such as an antibody and providing the antibody/alginic acid conjugate to a branched polymer such as PEG to form a hydrogel. The alginic acid-antibody conjugate is reacted with amine-terminated PEG molecules. In certain embodiments, the amine-terminated PEG molecule is a 4-arm PEG molecule. In other embodiments, the binding agent, antibody, and PEG are reacted at the same time to create an antibody/alginic acid/PEG hydrogel. In still other embodiments, the PEG and binding agent are conjugated. In these embodiments, the conjugate is reacted with alginic acid.

In some aspects, the methods further comprise utilizing protecting groups, such as fluorenylmethyloxycarbonyl (FMOC) groups, to achieve control over binding agent conjugation to primary amine groups. The methods also comprise adding the antibody/alginic acid/PEG hydrogels to a microfluidic device to coat the inner surface of the device.

In such embodiments, the hydrogel is allowed to form in situ and coats the inner surfaces of one or more chambers of the device.

Also disclosed are methods of separating cells from a complex medium using a microfluidic separator disclosed herein. In one aspect, the disclosure describe microfluidic devices comprising a substrate; and one or more chambers for receiving a sample comprising target biological materials, the one or more chambers comprise a surface coated with a hydrogel composition, the hydrogel composition comprising a plurality of alginic acid molecules and a plurality of polyethylene glycol molecules in which each of the polyethylene glycol molecule comprises a plurality of groups, at least one group of each polyethylene glycol molecule is conjugated to an alginic acid molecule and at least one other group of each polyethylene glycol molecule is conjugated to a binding agent. The devices disclosed herein further comprise a mixing chamber for mixing bound target biological materials with a neutralizing agent and one or more additional surfaces coated with a hydrogel composition. The hydrogel composition comprises a plurality of alginic acid molecules and a plurality of polyethylene glycol molecules in which each of the polyethylene glycol molecule comprises a plurality of groups and at least one group of each polyethylene glycol molecule is conjugated to an alginic acid molecule. Furthermore, at least one other group of each polyethylene glycol molecule is conjugated to a binding agent that is different from the binding agent in step (i).

Various substrate can be used in the disclosed devices. In some embodiments, the substrate is a silica-containing material (e.g., glass, PDMS). In some embodiments, the substrate is a polymeric material (both biocompatible and non-biocompatible), and the polymer is either bonded to itself or to other silica substrates. In some embodiments, the substrate is a thermosetting plastic, such as epoxies, including fiber-reinforced plastics. In some embodiments, the substrate is a metal (for example, gold, silver, platinum, copper, aluminum); metal alloy; metal oxide (copper oxide, aluminum oxide, silver oxide, indium tin oxide, etc.); an inorganic material, including but not limited to semiconductors and magnetic materials. In some embodiments, the substrate is a combination of the silica, polymeric, metallic, or inorganic materials described herein.

Microfluidic devices known in the art can also be utilized for the methods disclosed herein. The methods can be used to separate, for example, EPCs from blood for subsequent use in vascular tissue engineering or cell-based regenerative repair of vascular tissue in vivo. The methods involve allowing an alginic acid/PEG hydrogel to form in situ in a microfluidic device. The methods further entail providing a sample to the device and allowing the binding agent conjugated to the hydrogel to capture a target biological material, such as a particular cell type. The sample is allowed to pass through the device and the captured cells are released using a releasing agent. In certain embodiments, the releasing agent is a release buffer including, for example, a chelator such as ethylenediaminetetraacetic acid (EDTA), ethylene glycol tetraacetic acid (EGTA), and sodium citrate. In these embodiments, samples include but are not limited to whole blood, serum, saliva, lymph, bile, urine, and any other biological fluid.

In some aspects, methods of capturing and releasing target biological materials from a sample comprise providing a microfluidic device comprising one or more chambers for receiving fluids, wherein at least one of the one or more chambers comprises a surface coated with a hydrogel composition. The hydrogel composition comprises a plurality of alginic acid molecules and a plurality of branched polymer molecules in which each of the branched polymer molecule comprises a plurality of groups and at least one group of each branched polymer molecule is conjugated to an alginic acid molecule. Furthermore, at least one other group of each branched polymer molecule is conjugated to one or more binding agents. The methods further comprise introducing a sample comprising target and non-target biological materials into the one or more chambers under conditions effective to bind the target biological materials to the hydrogel composition and releasing the target biological materials using a releasing agent.

In some embodiments, the methods further comprise removing the unbound non-target materials from the sample.

In another aspect, methods of capturing and releasing target biological materials from a sample comprise (a) providing a microfluidic device comprising one or more chambers for receiving fluids, wherein at least one of the one or more chambers comprises at least one surface coated with a hydrogel composition. In some embodiments, the hydrogel composition comprise a plurality of alginic acid molecules and a plurality of branched polymer molecules, wherein each of the branched polymer molecule comprises a plurality of groups, at least one group of each branched polymer molecule is conjugated to an alginic acid molecule, and at least one other group of each branched polymer molecule is conjugated to one or more binding agents. Furthermore, the methods comprise (b) introducing a sample comprising target biological materials into a first chamber of the device under conditions effective to bind biological materials to the hydrogel composition; (c) releasing the bound biological materials using a releasing agent; and (d) contacting the releasing agent with a neutralizing agent to neutralize the releasing agent in a second chamber. In certain embodiments, the methods entail (e) providing the contents of the second chamber into a third chamber comprising a surface coated with the hydrogel composition, wherein the binding agent in the third chamber is a different binding agent than that used in (a), under conditions effective to bind the target biological materials to the hydrogel composition; and (f) releasing the bound, target biological materials using a releasing agent.

Figure 11:
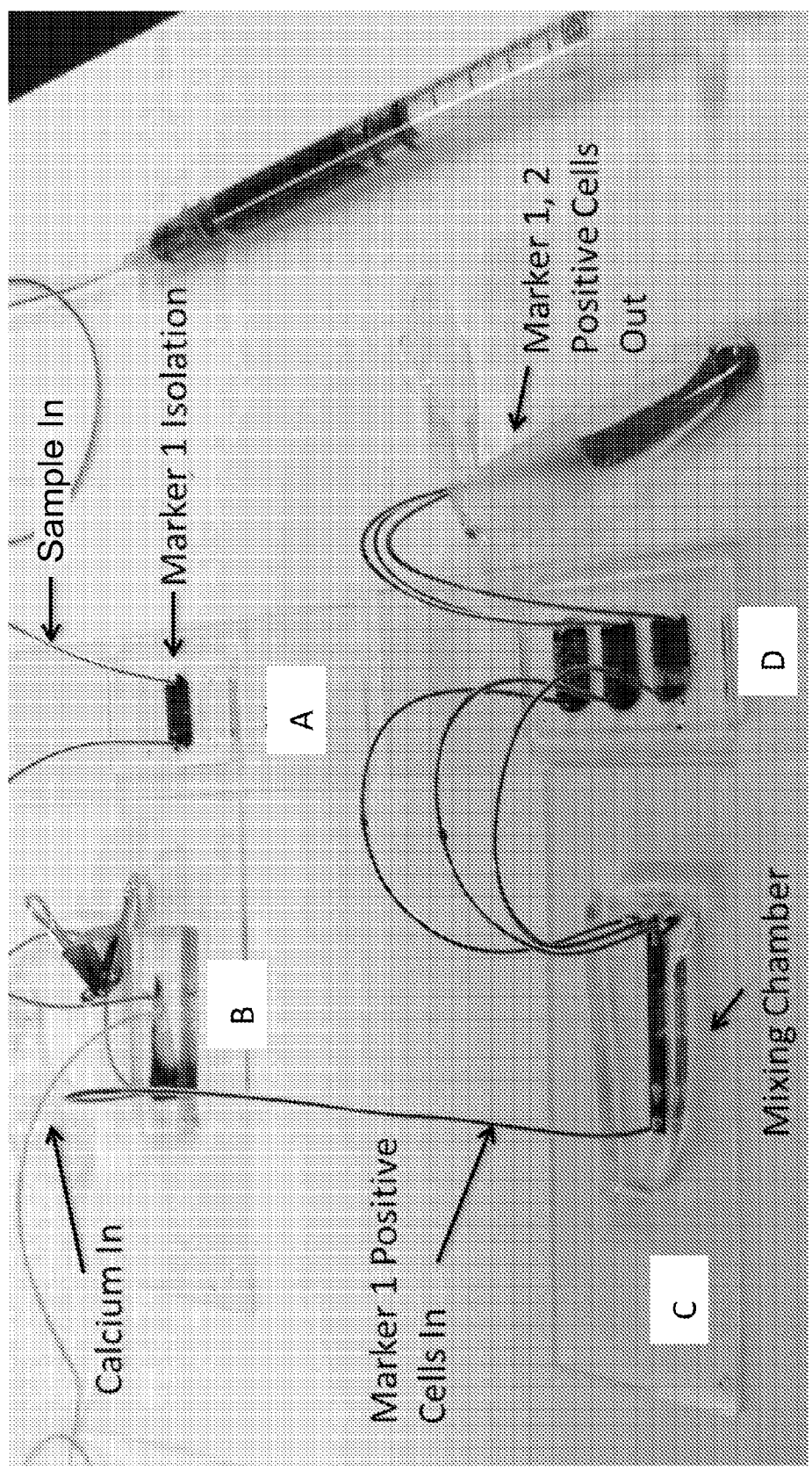

FIGS. 11A-D illustrate the devices and methods using multiple chambers. In FIG. 11A-D, a sample was injected via a syringe pump into the first alginate-based capture stage ("Marker 1 isolation"/FIG. 11A). This stage was connected to stage B, which was a 2-way valve. In its "closed" configuration, this valve allowed the waste from stage A to pass through to a collection tube. After the waste went through, the waste stream was closed using, for example, a pinch valve. (FIG. 11B). The purpose of the calcium chloride was to neutralize the EDTA in the cell suspension emerging from stage (FIG. 11A). To ensure mixing of the calcium chloride solution with this cell suspension, the combined output (which was in laminar flow) was sent into a mixing chamber (FIG. 11C) containing herringbone features. The mixed solution then entered stage (FIG. 11D), where the cells expressing receptors for the second capture molecule were captured. The final step in the separation process was the injection of an EDTA solution into the stage A (FIG. 11A) inlet, which releases the captured cells from stage B (FIG. 11B). This solution was collected in a tube containing an excess of culture medium to minimize any deleterious effect of the EDTA on the cells.

In some embodiments, the methods further comprise adding culture medium to the released biological materials.

In some embodiments, (d) through (f) can be repeated using a different binding agent. In some embodiments, the methods further comprise detecting the target biological materials after release from the hydrogel composition. In some embodiments, the methods further comprise maintaining the cells under conditions effective to culture, detect, analyze, or transform the cells, including living cells.

In some embodiments, the cells are rare cells, including but not limited to adult stem cells, fetal stem cells, progenitor cells, peripheral hematopoietic stem cells, endothelial progenitor cells, circulating tumor cell, mature circulating endothelial cells, amniotic stem cells, mesenchymal stem cells, adipose-derived stem cells, intestinal stem cells, skin stem cells, neural stem cells, and cancer stem cells. In some embodiments, the cell is a living cell captured from the sample. In some embodiments, the chelating agent is selected from the group consisting of EDTA, EGTA, and sodium citrate.

FIGS. 4A-C illustrates various synthetic methods for the production of hydrogels (designated gel types I through VII). The progressive improvement in EPC capture yield and purity from gel type II-VII is shown. In FIG. 4A, all reagents (including PEG, antibody, alginic acid) are combined together in gel types II-IV. In FIG. 4B, Gel Type V utilizes a two-step protocol in which the PEG, antibody, EDC, and sulfo-NHS are combined in a single first step. In FIG. 4C, Gel Types VI-VII has pre-mixing of PEG and antibody prior to mixing other components. Pre-mixing allows optimal dispersion of antibody molecules among the PEG chains.

Figure 3B:
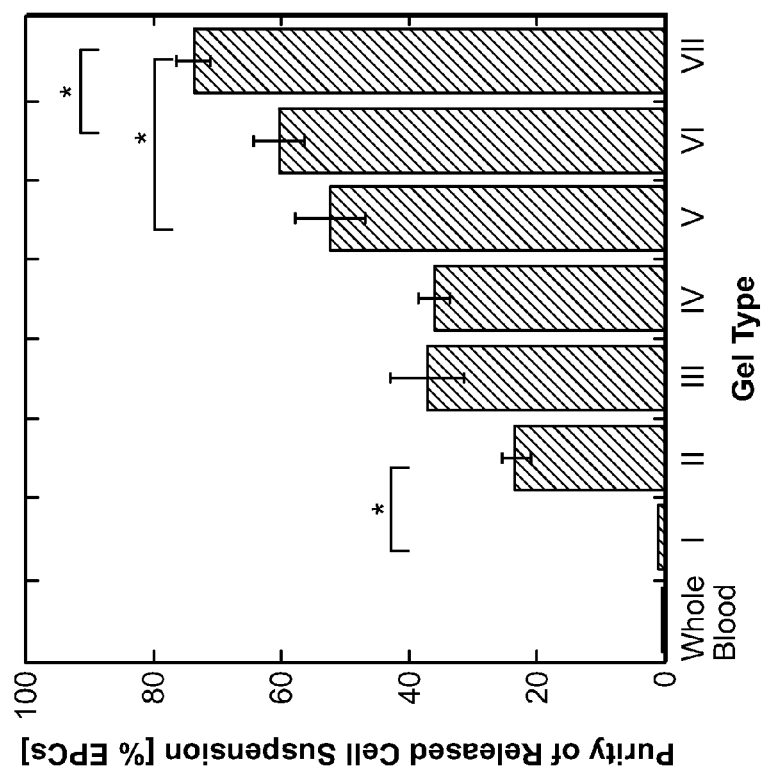
FIG. 3B is a diagrammatic representation showing the purity of EPCs captured from whole blood within microfluidic devices coated with PEG- and antibody-functionalized hydrogels.
Figure 3A:
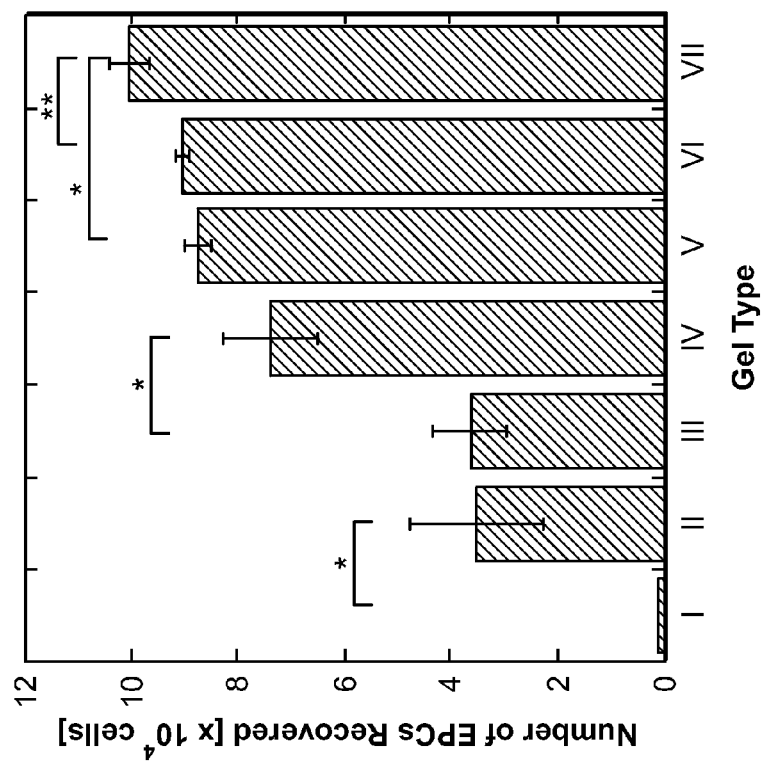
FIG. 3A is a diagrammatic representation showing the yield of endothelial progenitor cells (EPCs) captured from whole blood within microfluidic devices coated with PEG- and antibody-functionalized hydrogels.

The adhesive effect of the anti-CD34 antibody is evident by comparing gel types I and II (FIG. 3A). FIG. 3A-B depict results after 300 μL of whole blood collected in heparin tubes was directly injected into individual microfluidic devices, and 10 devices were run in parallel. Cells released from each device were pooled into a single suspension to allow enumeration by flow cytometry. Data reported represent yield and purity for EPCs recovered from a total blood volume of 3 mL. Error bars denote standard deviations based on 3 independent measurements of EPC and total cell counts made with the same sample. Increased yield and purity were observed with the incorporation of 10 k MW PEG (gel types II vs. IV). The methods and compositions disclosed can also be used with 20 k MW PEG, as well as other molecular weight PEG molecules so long as size constraints, such as steric forces, do not affect cell binding efficiency.

Figure 2:
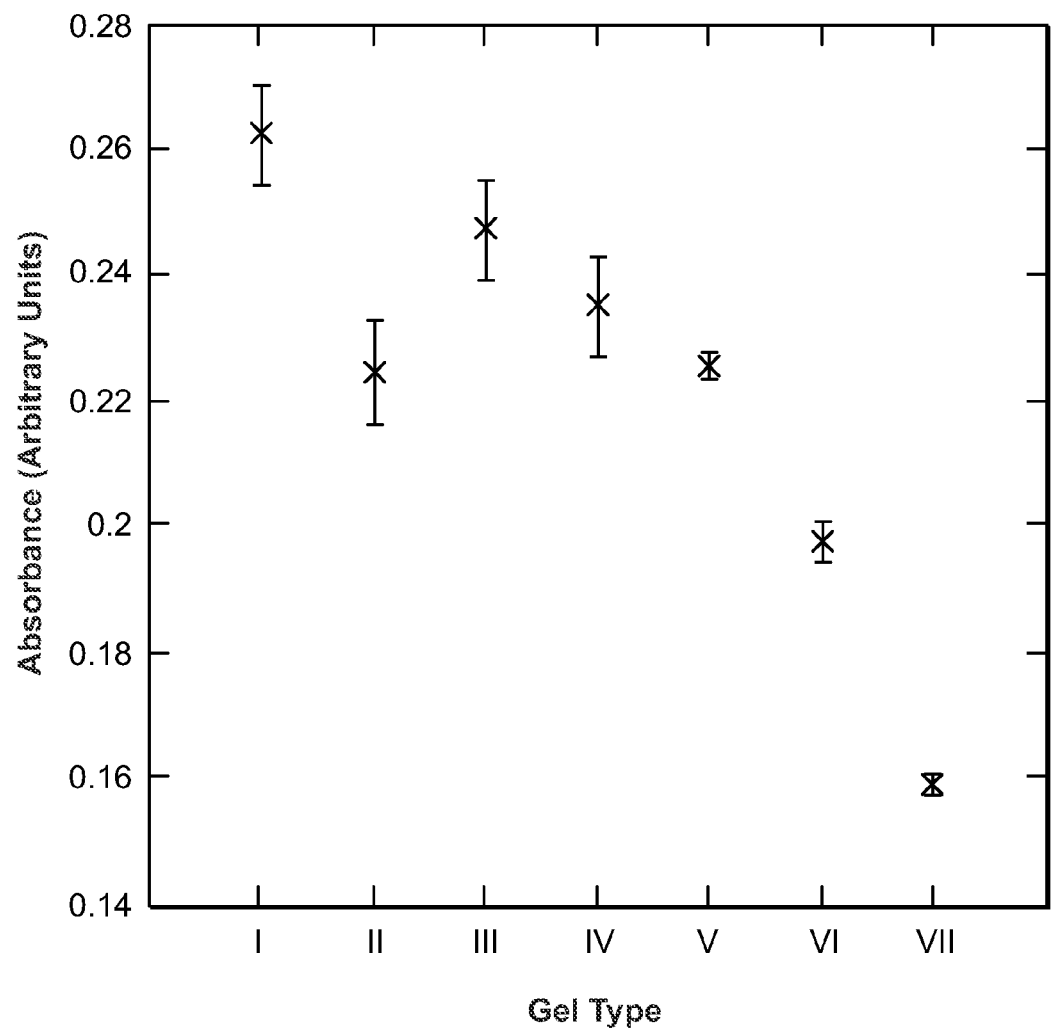
FIG. 2 is a diagrammatic representation of a qualitative measurement of accessible antibody within hydrogel-coated microfluidic devices.

In FIG. 4B, the first step in the synthesis was the combination of PEG and antibody with the coupling agents EDC and sulfo-NHS prior to the addition of alginic acid in the second step. Relative to gel type IV, gel type V provides slightly greater EPC capture but with a lower degree of scatter, indicating better mixing of the antibody molecules with the PEG. The accessible antibody content of gel type V is similar to that of gel type IV (FIG. 2), demonstrating that better PEG-antibody mixing is the distinguishing factor. In FIG. 2, a bicinchoninic acid (BCA) assay kit was utilized to measure the relative amount of antibody accessible to a solution flowing through each device. A lower absorbance is associated with a greater amount of accessible antibody. Error bars denote standard errors based on 8 independent measurements for each gel type. Better mixing also allows for more effective interspersing of PEG and antibody molecules on the hydrogel surface, which is consistent with the higher EPC purity obtained with gel type V relative to gel type IV. Fewer PEG particles were observed in the PEG- and antibody-functionalized alginic acid solution, which is consistent with better PEG-antibody mixing.

The two-step synthesis protocol for gel types VI and VII allows for pre-mixing by providing time for antibody and PEG molecules to mix 'undisturbed' without the constraining presence of EDC and sulfo-NHS. Although pre-mixing is not necessarily required for the methods and compositions disclosed herein, longer mixing time can improve EPC capture performance in terms of yield and purity, as can be seen when comparing gel types VI and VII to gel type V. The longer mixing and incubation times provided for gel type VII relative to gel type VI provided the good yield (~$10^4$ EPCs recovered) and purity (74%) as well.

Equivalents

Those skilled in the art will recognize, or be able to ascertain, using no more than routine experimentation, numerous equivalents to the specific embodiments described specifically herein. Such equivalents are intended to be encompassed in the scope of the following claims.

EXAMPLES

Example 1—Microfluidic Capture and Release Design

Example 1 describes methods and compositions for the highly specific capture and release of biological materials, such as cells.

Materials and Instrumentation

Glass slides, EDC, Sulfo-NHS, EDTA, MES buffer, a micro bicinchoninic acid (BCA) Protein Assay Kit and heparin vacuum tubes were purchased from Fisher Scientific (Fair Lawn, N.J.). For microfluidic device fabrication, SU-8 photoresist and developer were obtained from MicroChem (Newton, Mass.); silicone elastomer and curing agent were obtained from Dow Corning (Midland, Mich.). Phosphate-buffered saline (PBS; 1×, without calcium or magnesium) was purchased from Mediatech (Herndon, Va.). The capture antibody, monoclonal mouse anti-human CD34, and goat anti-human FLK-1 were obtained from Santa Cruz Biotechnology (Santa Cruz, Calif.). Anti-human CD133-PE, anti-human CD45-FITC, and anti-goat IgG-PerCP antibodies were obtained from eBioscience (San Diego, Calif.). Rabbit IgG was purchased from Vector Labs (Burlingame, Calif.). Calcium chloride dihydrate and alginic acid were purchased from Sigma (St. Louis, Mo.). Amine-terminated 4-arm PEG (PEG-NH2) with molecular weights of 10,000 (10 k MW) and 20,000 (20 k MW) were purchased from Laysan Bio (Arab, Ala.).

Microfluidic Cell Capture Device Design

The device used a post array design similar to that used by Nagrath et al, *Nature*, 450 (7173), 123-U10 (2007). To achieve disruption of flow streams and achieve optimal capture, the posts were arranged in a hexagonal layout as described by Gleghorn et al, *Lap Chip*, 10(1), 27-29 (2010). The posts had a diameter of 100 μm and a transverse spacing of 150 μm from center to center. Rows had a center to center spacing of 125 μm and each is offset by 50 μm. The post array was 0.7 cm long and 0.5 cm wide. The posts heights were approximately 50 μm for the devices fabricated by soft lithography as described below.

For poly(dimethyl siloxane) (PDMS) device fabrication, the silicone elastomer and curing agents were mixed in a 10:1 (w/w) ratio and poured on top of the negative master wafers, degassed, and allowed to cure overnight at 65° C. PDMS replicas were then pulled off the wafers prior to punching inlet and outlet holes with a 19-gauge blunt-nose needle. The replicas and glass slides were exposed to oxygen plasma (100 mW with 8% oxygen for 30 s) in a PX-250 plasma chamber (March Instruments, Concord, Mass.) and immediately placed in contact with each other. The irreversible bonding between PDMS and glass was completed by baking for 5 min at 65° C.

PEG/Antibody-Functionalized Hydrogel Synthesis

Seven different hydrogel formulations were investigated in this study, and these are designated as Gel Types I-VII. For Gel Type I, 45 mg of alginic acid, 4.8 mg EDC, 13.2 mg sulfo-NHS, and 20 µL inert IgG (1 g/mL) were added to 2 ml of MES buffer solution and mixed using an IKA Ultra Turrax Tube Disperser for 29 min and allowed to incubate for 60 min. For Gel Type II, 45 mg of alginic acid, 4.8 mg EDC, 13.2 mg sulfo-NHS and 100 µL anti-human CD34 (200 m/mL) were added to 2 mL of MES buffer, mixed as before, and incubated for 60 min. For Gel Type III, 45 mg alginic acid, 4.8 mg EDC, 13.2 mg sulfo-NHS, 22.5 mg 20 k MW PEG, and 100 µL anti sheep CD34 were added to 2 mL of MES buffer, mixed for 29 min, and allowed to incubate for 60 min. Gel type IV consisted of 45 mg alginic acid, 4.8 mg EDC, 13.2 mg sulfo-NHS, 22.5 mg 10 k MW PEG, and 100 µL anti sheep CD34 added to 2 mL of MES buffer, mixed for 29 min and allowed to incubate for 60 min. Gel Type V was created by mixing 4.8 mg EDC, 13.2 mg sulfo-NHS, 22.5 mg 10 k MW PEG, and 100 µL anti sheep CD34 in 2 ml of MES buffer for 29 min and then adding 45 mg of alginic acid followed by 29 min of mixing and 60 min of incubation. Gels VI and VII were formed by mixing 22.5 mg 10 k MW PEG with 100 µL antibody in 2 mL of MES buffer and mixing for 10 min and 29 min, respectively, and incubating for an additional 15 min and 60 min, respectively. 4.8 mg EDC, 13.2 mg sulfo-NHS, and 45 mg alginic acid were then added to the mixture, mixed for 29 min and allowed to incubate for 60 min.

Following the incubation step, each functionalized alginic acid solution for each gel type was injected into a Slide-A-Lyzer Dialysis Cassette 10,000 molecular weight cut-off (Fisher) and dialyzed against MES buffer for 48 hours to remove unreacted sulfo-NHS and EDC. Table 1 summarizes the synthetic steps and components for each gel type. Steps 1 and 2 indicate the sequential nature of the protocol followed for combining the respective reagents.

TABLE 1

Summary of Synthesis Protocols for Different Hydrogel Formulations.

| Gel Type | PEG MW [kDa] | Alginic Acid | EDC & Sulfo-NHS | PEG | Antibody* | Mixing/Incubation Times [min] Step 1 | Step 2 |
|---|---|---|---|---|---|---|---|
| I | none | 1 | 1 | — | 1 | 29/60 | N/A |
| II | none | 1 | 1 | — | 1 | 29/60 | N/A |
| III | 20 | 1 | 1 | 1 | 1 | 29/60 | N/A |
| IV | 10 | 1 | 1 | 1 | 1 | 29/60 | N/A |
| V | 10 | 2 | 1 | 1 | 1 | 29/0 | 29/60 |
| VI | 10 | 2 | 2 | 1 | 1 | 10/15 | 29/60 |
| VII | 10 | 2 | 2 | 1 | 1 | 29/60 | 29/60 |

†"1" denotes reagent added in step 1; "2" denotes reagent added in step 2.
*Inert IgG was used for Gel Type I; anti-human CD34 was used in all other gel types.

Infrared Spectroscopy

Functionalized alginic acid samples were spread on poly(tetrafluoroethylene) (PTFE) sample cards (Crystal Labs, Garfield, N.J.) using a spatula and allowed to thicken for 4 hours. The cards were then inserted into a Perkin Elmer 1000 Fourier-transform Infrared (FTIR) spectrometer. The absorbance at 638 cm$^{-1}$ was analyzed and compared for each gel type. This peak, which is associated with amide bonds formed when antibody molecules are successfully conjugated to the PEG-NH$_2$, is a measure of antibody loading in the hydrogels.

In Situ Hydrogel Formation within Microfluidic Devices

A 1 g/mL solution of CaCl$_2$ in deionized water was injected into each device (by hand, using a 1 mL syringe) and allowed to incubate overnight. The CaCl$_2$ solution was then withdrawn by hand using a 1 mL syringe. The PEG- and antibody-functionalized alginate solution prepared for each gel type was then injected into the devices by hand and allowed to adsorb for 1 hour. Next, the devices were rinsed with MES buffer at 10 µl/min for 10 min using a Harvard Apparatus PHD 2000 syringe pump (Holliston, Mass.), followed by a 100 mM CaCl$_2$ solution in MES buffer at 10 µl/min for 10 min to form a thin layer of hydrogel on the walls of the microchannels. Finally, the devices were rinsed with MES buffer at 5 µl/min for 10 min to remove unreacted CaCl$_2$.

BCA Protein Assay

A BCA protein assay solution was prepared according to manufacturer instructions. The solution was then injected into each device at 5 µl/min for 40 min. The output was collected in a microplate and absorption at 562 nm was measured using a Bio-Tek Powerwave XS spectrometer.

Blood Draw

Whole human blood was drawn from healthy volunteers in heparin collection tubes under a protocol approved by the Northeastern University Institutional Review Board.

EPC Capture Experiments

Whole blood was injected into microfluidic capture devices at 5 µl/min for 60 min. Each device was then rinsed with MES buffer at 10 µl/min for 5 min. For release of captured cells, a 50 mM solution of EDTA in PBS was injected at 10 µl/min for 10 minutes and the output was collected in a 1.5 mL microcentrifuge tube. Each individual experiment included 10 microfluidic devices. 300 µL of blood were passed through each device, at the rate specified above. The cells released from each device were pooled into a single suspension to allow enumeration by flow cytometry. The data reported in FIG. 3A-B represent yield and purity for EPCs recovered from a total blood volume of 3 mL.

Flow Cytometry

For EPC enumeration, cells released from each device were mixed with 10 µl each of anti-human CD133 PE, anti-human CD45 FITC, anti-goat FLK-1, and anti-goat IgG PerCP. The mixture was stored in the dark for 30 min and centrifuged at 130×g for 10 min. The supernatant was decanted and cells were suspended in 200 µL of PBS for enumeration using a Beckman Coulter Cell Lab Quanta SC flow cytometer. Cells that were CD133+, CD45−, and FLK-1+ were counted as EPCs.

Results

Figure 1:
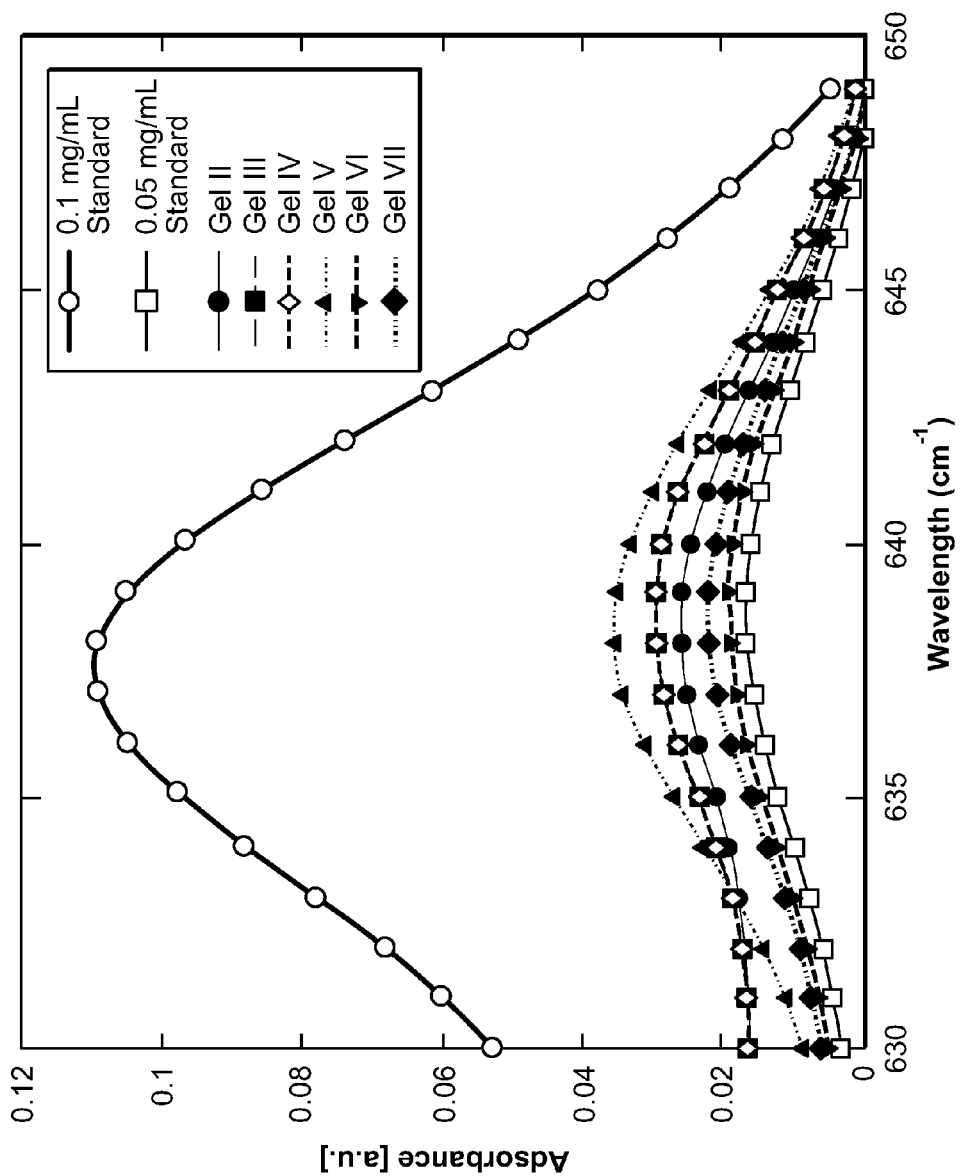
FIG. 1 is a diagrammatic representation of an infrared spectra of PEG- and antibody-functionalized hydrogels (Gels II-VII) compared to a standard solution of antibody (0.1 mg/ml and 0.05 mg/ml antibody). Note that the measurement is a bulk measurement.

FIG. 1 shows infrared spectroscopy data for quantification of antibody loading within the functionalized alginic acid solutions emerging from the one- or two-step synthesis protocol. When compared to standard solutions of known anti-CD34 concentration, all of the alginic acid solutions have comparable antibody content between 0.05 and 0.06 mg/mL.

FIG. 2 shows the relative total protein measurements made using a BCA assay kit. The BCA solution becomes more transparent as it comes in contact with proteins such as antibodies. Hence, by flowing this solution through hydrogel-coated microfluidic devices, the amount of accessible antibody on each gel type can be compared. The protein content of the solutions exiting the devices is shown as a function of gel type in FIG. 2 and is expressed in arbitrary units of absorbance rather than as a calibrated mass or concentration. The relative measurement allows comparison of the accessible anti-CD34 capture antibody between each gel type. FIG. 2 shows an increase in accessible antibody from gel types I-VII while the total amount of antibody added to the mixture remains constant (FIG. 1), indicating an increase in the efficiency of conjugation between the gelled surface and the antibody.

FIG. 3 shows yield and purity data for the capture of EPCs from whole blood using the hydrogel-coated microfluidic devices. In FIG. 3A, gel type I, which has an inert antibody conjugated to it, shows negligible EPC adhesion as expected. Gel type II, which contains the anti-CD34 antibody, shows significantly higher EPC adhesion relative to gel type I ($p<0.005$), albeit with a high degree of scatter. The purity of capture achieved with gel type II is, however, relatively low (~23%; FIG. 3B). The effect of adding the 4-arm PEG to the hydrogel structure is shown clearly by comparing gel types II and IV, whose synthesis protocol is otherwise identical. The branched amine termini of the 4-arm 10 k MW PEG molecules provide an opportunity for a greater level of antibody conjugation, as reflected in the higher overall EPC adhesion (FIG. 3A). The suppression of non-specific binding results in an increase in purity (FIG. 3B; gel type IV). Interestingly, the use of 20 k MW PEG (gel type III) resulted in significantly lower EPC capture yield relative to 10 k MW PEG (gel type IV; $p<0.005$) under the same synthesis conditions and purity levels were comparable.

In gel types V-VII, a two step protocol for combining reagents was followed. In gel type V, the conjugation of the antibody molecules to the 4-arm PEG is carried out first before introducing alginic acid. This formulation improved yield and purity of EPC capture relative to gel type IV. The two-step protocol was modified such that EDC and sulfo-NHS were added in the second step with alginic acid and the first step was restricted to the mixing together of PEG and antibody. When short times were provided for mixing and incubation for the first step (10 min and 15 min, respectively, for gel type VI), the yield did not improve relative to gel type V, but purity was higher. Higher mixing and incubation times were examined next (29 and 60 min, respectively, for gel type VII) to achieve greater mixing and entanglement of the PEG molecules with the antibody molecules. This formulation provided significantly higher yields and purity relative to gel types VI and VII ($p<0.005$ and $p<0.01$, respectively).

Example 2—Microfluidic Capture and Release of Stem Cells Using GPR49/Lgr5 Receptors Example 2 discloses devices and methods for the microfluidic capture and release of intestinal stem cells using two binding agents, specifically, GPR49 and Lgr5 antibody receptors.

The push towards the investigating multi-potent and quiescent stem cells within the intestinal system has been prevalent in the recent years. (David, H. S. et al., Current View: Intestinal Stem Cells and Signaling. *Gastroenterology* 2008, 134 (3), 849-864.; Montgomery, R. K. et al., Prominin1 (CD133) as an Intestinal Stem Cell Marker: Promise and Nuance. *Gastroenterology* 2009, 136 (7), 2051-2054.). However, current methods have relied on hybridized mice models and fluorescent makers. This disclosure circumvents the need for fluorescent markers and cell sorting machines by implementing microfluidics coupled with affinity capture.

Characterizing and identifying intestinal stem cells have been under much scrutiny within the gastroenterology community. (Sangiorgi, E., et al., Bmi1 is expressed in vivo in intestinal stem cells. *Nat Genet* 2008, 40 (7), 915-920; Snippert, H. J. et al., Prominin-1/CD133 Marks Stem Cells and Early Progenitors in Mouse Small Intestine. *Gastroenterology* 2009, 136 (7), 2187-2194; Bjerknes, M. et al., Intestinal epithelial stem cells and progenitors. *Method Enzymol* 2006, 419, 337-383; Barker, N., et al., The intestinal stem cell. *Gene Dev* 2008, 22 (14), 1856-1864.)

Conflicting models on where these cells reside in the crypt zone have been constrained to a +4 Label retaining cell (LRC) model and a crypt based columnar cell (CBC) model. Until recently, the characterization markers for the intestinal stem cell populations relied on BMI-1, Mushashi-1, and other quiescent and active cycling markers constricted to the intracellular domain. Barker et al. has discovered a gene which codes for active cycling intestinal stem cells resides in a receptor known as a leucine coupled G-protein receptor (Lgr5). (Barker, N., et al., Identification of stem cells in small intestine and colon by marker gene Lgr5. *Nature* 2007, 449 (7165), 1003-U1). Over expression these gene in hybridized mice coupled with GFP-FACS sorting, allowed for in vitro culture systems to be developed and genomic analysis of these cell types. Sato, T., et al., Single Lgr5 stem cells build crypt-villus structures in vitro without a mesenchymal niche. *Nature* 2009, 459 (7244), 262-U147). Utilizing commercially available antibodies allowed for extracellular staining of these stem cell subtypes targeting the Lgr5 receptor. (Olsen Hult, L. T., et al., EP Receptor Expression in Human Intestinal Epithelium and Localization Relative to the Stem Cell Zone of the Crypts. *PLoS One* 2011, 6 (10), e26816). Implementing these antibodies allow for a selective capture and release of these target cells utilizing alginate functionalized with antibodies from wild-type rat tissue.

Conversely, this Example allows for multiplexing and larger sample volume to be processed while retaining viability of the eluded target population. In previous studies by other groups, culture methods have been developed to induce hyperplasia and organoid forming units derived from single cells. (Sato, T. et al., Single Lgr5 stem cells build crypt-villus structures in vitro without a mesenchymal niche. *Nature* 2009, 459 (7244), 262-U147). These cells do not require a mesenchymal niche to develop into these units and rely on growth factors to induce differentiation cues. It has been reported that lgr5 cells in culture have a 6% plating efficiency (Sato 2009); recent developments have alluded to necessary wnt signaling via Paneth cells to improve plating. (Sato et al., Paneth cells constitute the niche for Lgr5 stem cells in intestinal crypts. *Nature* 2011, 469 (7330), 415-+).

In this Example, enriched lgr5 positive populations have been captured and released using the methods disclosed, and the cells yielded similar morphological responses as produced by previous groups. Furthermore, the addition of wnt3a in culture facilitated an increase in plating efficiency. Immunohistochemical analysis coupled with confocal microscopy shed light on lgr5 and cd24 expression within the central lumen coinciding with recent reports. (See Gracz, A. D. et al., Sox9 expression marks a subset of CD24-expressing small intestine epithelial stem cells that form organoids in vitro. *Am J Physiol-Gastr L* 2010, 298 (5), G590-G600.).

In this Example, with the alginate hydrogel having covalently bound antagonistic GPR49/Lgr5, the capture and release mechanism resides in cross-linking the hydrogel with calcium with a chelation release. This Example demonstrates the ability to selectively capture and release GPR49/Lgr5 positive cells from wild-type rat colon crypts digestate. Through a one-pass approach, a 24-fold enrichment from the starting suspension to a final purity of 49% GPR49/Lgr5 cells was obtained. The presented microfluidics platform retains viability of the target cells, while giving the end user the ability to multiplex samples. The disclosure allows for intestinal stem cell isolation that has the potential in advancing the field of tissue engineering and applications with co-cultures.

Methods

Animals

Male and female neonatal Lewis rats (Charles River) were used and harbored in room temperature conditions with a 12-hour light/dark cycle following U.S. Eastern Standard Time. For the progenitor cell isolation studies, neonatal rats between the ages of 2 to 5 days were utilized and sacrificed via decapitation. All studies and protocols were approved by the Institutional Animal Care and Use Committee (IACUC) at Northeastern University.

Tissue Digestion

Intestinal tissue samples were obtained from neonatal Lewis rats. Large intestine was extracted, split laterally, and fragmented into 1 mm segments. Fragmented tissue was incubated in 2 mM EDTA at 4° C. for 30 minutes. Tissue samples were separated from the solution and placed in 20 mL of phosphate buffered saline (PBS, Gibco) for 10 minutes of agitation. The supernatant fluid was then collected and centrifuged at 150×g for three minutes; the pellet was collected, suspended in 10 mL of serum-free Dulbecco's Modified Eagle's Medium (DMEM, Cellgrow) and centrifuged again at 150×g. The pellet was suspended in 5 mL of serum-free DMEM solution and filtered through a 100 µm cell strainer. The solution was then filtered through 20 µm cell strainers into 1 mL eppendorf tubes.

Microfluidic Cell Isolation Device Fabrication

Microfluidic devices were fabricated using traditional soft lithography at the George J. Kostas Nanoscale Technology and Manufacturing Research Center at Northeastern University. The physical dimensions and design of the devices were identical to those of devices described by Hatch et al. These devices consist of polydimethylsiloxane (PDMS) patterned with 100 µm diameter pillars bonded to glass slides.

Alginate Formulation

Antibody-functionalized alginate reaction underwent six different scenarios but stoichiometric ratios of reagents remained constant through out each scheme. 1940 µL, MES (Thermo-fisher), 0.04 mg Anti-GPCR GPR49 (Abcam), and 22.5 mg 10 KD 4-arm star PEG ( ) was mixed for 30 minutes. MES pH was altered for each respective scenario which was either held at ph 4.7 or 6.0; the pH was titrated with NaOH to a pH of 6.0. The amalgam was allowed to incubate for 60 minutes in scenario II, but the subsequent reagents were added immediately in the remaining scenarios. 13.8 mg sulfo-NHS (pierce), 4.8 mg EDC (pierce), and 45 mg alginate (thermo) was added, allowed to mix for 60 minutes, and incubated for another 60 minutes in scenario II. The functionalized alginate was injected into a 10 KD dialysis cassette (Thermo) and suspended in its dilate, MES, at its respective scenario pH for 48 hours.

Channel Formation, Injection, and Release

Microfluidic devices with a hexagonal post array were utilized for cell separation. Each device was filled with alginate functionalized with Anti-GPCR GPR49 and allowed to incubate for 60 minutes. Channels were formed by flowing through 100 µL of pH 6 MES buffer at 10 µL/min, 100 µL of 100 mM $CaCl_2$ at 10 µL/min, and 100 µL of 0.1% bovine serum albumin at 10 µL/min. A Harvard Apparatus syringe pump was used to obtained precise flow rates. Cell solutions obtained were mixed to ensure homogenous suspension and 200 µL were drawn into 1 mL syringes. 100 µL of cell solution was pumped through each device at a rate of 3 µL/min followed by 100 µL of pH 6 MES buffer at 3 µL/min to rinse. Then 100 µL of 100 mM EDTA solution was pumped through the device at 10 µL/min to release the cells from the device. For culture, cells were released into eppendorf tubes containing 50 µL of Matrigel (BD Bioscience) on ice.

Flow Cytometry

Flow cytometry analysis of both the starting (i.e. tissue digestate) cell suspensions and the isolated cells was performed using a Beckman Coulter Quanta SC flow cytometer. Anti-GPCR GPR49-RPE was used to quantify injected and released populations. Primary and secondaries were diluted 1:50 in PBS, respectively.

Cell Culture

The enriched stem cell population was mixed with the matrigel after release and each sample was plated into a well plate and incubated for 10 minutes at 37° C. Lgr5 basal media contained the following constituents: Advanced DMEM F-12, 5 ml N2 supplement, 10 mL B27 without vit. A, 5 mL HEPES, 6.25 mL glutamax. Each sample was rinsed with 350 µL of Lgr5 basal media in to remove EDTA from the cell culture. Then 17 µL of ROCK inhibitor (y-27632, Sigma-Aldrich) was added to 10 mL of Lgr5 media. 486 µL of this solution was added to each well plate along with growth factors to the following concentrations: 100 ng/mL of murine Noggin (Peprotech), 100 ng/mL of murine Wnt3A (Peprotech), 50 ng/mL of rat EGF (Peprotech), and 1 µg/mL of murine Rspondin-1 (R&D Biosciences). After each growth factor was added, the samples were moved into a humidity chamber kept at 37° C., 5% $CO_2$. After two days of cell growth, the media was refreshed. The spent media is removed and Lgr5 media, without ROCK inhibitor, is added to each well plate. Growth factors were added to the following concentrations: 100 ng/mL of Noggin, 100 ng/mL of Wnt3A, 50 ng/mL of EGF, and 500 ng/mL of Rspondin-1.

Immunohistochemical Staining of Organoids

Enriched organoids were fixed with 4% paraformadahyde and rinsed with 2 mM glycine in PBS. 6 U/ml dispase (stem cell technologies) was added and incubated for 1 hour to release organoids from matrigel. Organoids were pipetted into 200 µL Lgr5 media blocking solution containing: 3% BSA, 10% goat serum, 0.1% triton X-100, 10 mM HEPES, and 10 mM glycine. 1:50 of respective antibodies, anti-GPCR GPR49 and anti-CD24, to blocking solution was added and incubated at 4° C. overnight. Organoids were pipetted out of solution and into 200 µL of blocking solution containing normalized concentrations of Alexfluor 488, Alexafluor 568, and 0.5 µg/ml DAPI for 3 hours. Organoids were mounted on glass cover slides and confocal images were taken via Nikon confocal microscope.

Results

Microfluidic Enrichment of Intestinal Stem Cells

Figure 6C:
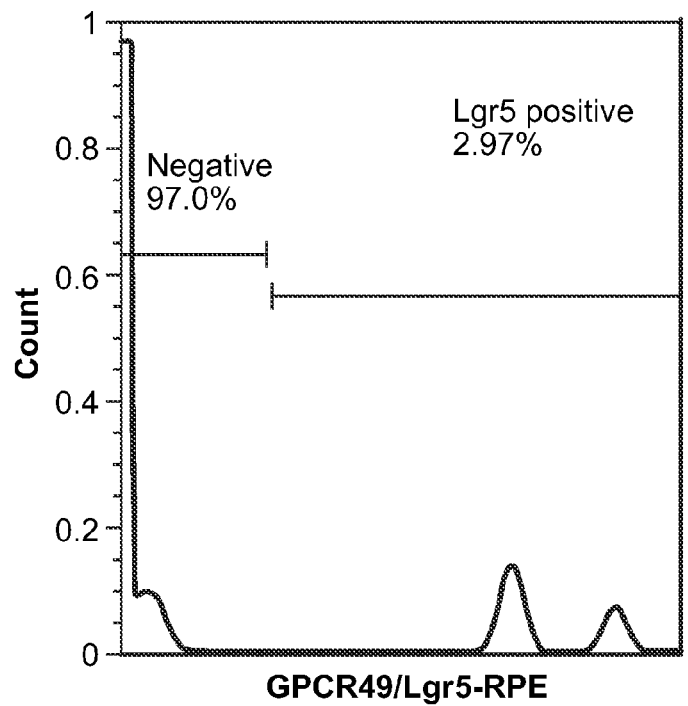

Modifications to the experimental parameters, including adjusting reaction pH and pacification, were needed to increase the fold Lgr5 enrichment and purity (FIG. 6A). The samples and formulations were divided into five scenarios (FIG. 6A), each varying one variable. The purity yield of these scenarios were compared against the injected population. Quantization the percent purity was preformed via flow cytometry against the injected (FIG. 6C) and the released (FIG. 6C). Each histogram was gated from the EV vs. side scatter regime to midicagate noise and each gate was propagated through each sample. *P<0.0005, P<0.001, *P>0.05; n=3. Optimizations for Lgr5 capture encompassed four variables including flow rate, pacification, pH, and reaction time. Bovine serum albumin (BSA), a pacifying agent, allowed for a decrease in fouling within the microfluidics channels, which facilitated establishment of consistent flow across the channel and inhibition of non specific binding to the alginate/antibody conjugate. Concentration of BSA, varied in procedures IV and V, had little effect on the system and did not affect purity yields (FIG. 6B). Flow rates, adjusted between 3 and 5 µL/min (scenario III and IV), resulted in a fairly significant disparity in which alluded to possible shear effects upon the target cells at higher flow rates (FIG. 6B).

PH affects within the alginate reaction were investigated to improve 4-arm star PEG, EDC, and antibody interactions. In comparing scenarios III and VI, it is evident that a pH change from 4.7 to 6.0 had a significant overall affect on efficacy of the alginate hydrogel in capturing Lgr5 positive cells (p<0.001). Increasing the pH deprotenates reaction sites, thus allowing an increase in reaction potentials of antibody-PEG and alginate-EDC conjugates and driving the overall reaction to completion. Mixing and incubation times had no statistically significant effect in enrichment. Scenario III resulted in the greatest purity yield, with approximately 49% pure population of Lgr5 positive cells released; this formulation facilitated a 24-fold lgr5 enrichment from injected suspension (FIG. 6B). Viability was assessed with the microfluidics approach and yielded approximately 85% viable retention (data not shown).

Validation and Enumeration of Lgr5 Positive Cells Via Flow Cytometry

Figure 6D:
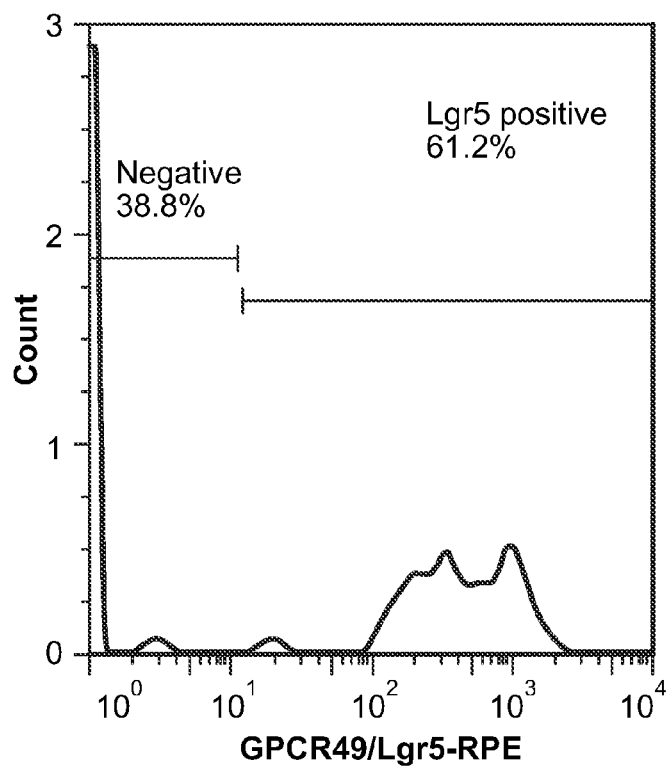

To determine the enrichment capabilities and purity yields post-microfluidic device, flow cytometry was used to enumerate positive populations with respect to different alginate/antibody formulations. Initial gating within the side and forward scatter regime allowed for mitigating extraneous debris. Injected and released intestinal digestate suspensions were conjugated with anti-GPCR GPR49-RPE in PBS. Control populations, absent of an antibody tag, were run in the same fashion to allow for mediation of noise and auto-fluorescence. Injected and released populations were gated in the same fashion and overlaid against the control to compensate for noise. The injected samples comprised of approximately 2.3% Lgr5 positive cells from the intestinal digestate (FIG. 6C). The flow cytometry analysis illustrated a 24-fold enrichment of the target Lgr5 positive population relative to the released in scenario III (FIG. 6D).

Enriched Cells Induced Hyperplasia and Singe Cell Derived Organoids

Released enriched Lgr5 positive cells were imbedded in Matrigel and grown under similar conditions as described in Sato et al.; Single Lgr5 stem cells build crypt-villus structures in vitro without a mesenchymal niche. *Nature* 2009, 459 (7244), 262-U147. The culture technique for lgr5 positive cells included growth factor constituents that were altered slightly to take into account species dependent factors. Rat endothelial growth factor (EGF) and murine rspondin-1 were used, in contrast to the literature sources that have implemented a hybridized mouse model. Y-26743, rock inhibitor, was used to improve culture stability and to prevent anoikis in a single cell suspension. The inhibitor was also used concurrently in the microfluidic enrichment technique, and it was observed to result in an increase in plating efficiency (data not shown), but exhibited little affect in unenriched cultures (FIG. 7A-C). Progression of organoids, from enriched single lgr5 cells, was viewed up to 4 days and compared against an unenriched population (FIG. 7D-E). Growth was noticed at day 2 and progressed into hyperplasia stage at day 3. Small lumen formation coupled with an increase of hyperplasia is observed at day 4.

FIG. 7A-C show that unenriched organoid progression yielded significant larger cyst-like organoids surrounded by extraneous populations. FIGS. 7D-F show four-day progression of enriched organoid derived from single cell suspension. Expansion of single cell (FIG. 7D) at day 2, induced hyperplasia at day 3 (FIG. 7E), and small lumen formation noticed with surrounding secreted apoptotic cells, at day 4 (FIG. 7F) are shown. Scale bars represent 100 µm The day progressions of the released lgr5 positive cells were cultured in parallel against an unenriched population. The unenriched suspension was seeded at the same volume as the released population and cultured under the same conditions. Multiple morphologies were apparent in the unenriched culture, ranging from organoids with central lumen, harboring apoptotic cells (FIGS. 7C and 8C), to fibroblastic morphologies. Growth rate of the un-enriched suspension was more accelerated in comparison to the enriched population. Plating efficiency was improved amongst the enriched population by the addition of Wnt3a to the culture system (FIG. 8B). The addition of wnt3a to culture medium sustains viability and independence from paneth cell (FIG. 8D).

The unenriched population (FIG. 8A) did not have an any increase in plate efficiency in the presence of Wnt3a protein. The majority of the organoids formed in the injected culture expressed a cyst-like structure harboring apoptotic cells (FIG. 8C). Conversely, the enriched population (FIG. 8B) did have an increase in plating efficiency leading to more single derived organoids proliferating. Enriched cells exhibited similar morphology to the wnt3a absence study (FIG. 8D) at analogous time points. Images were taken at 3 days in culture; scale bar represents 100 µm.

Immunostaining of Enriched and Unenriched Organoids Via Confocal Microscopy

Enriched and unenriched organoids were released from culture at day 4 via a dispase treatment to degrade the Matrigel. Stained organoids were exposed to anti-GPR GPRCR49, anti-CD 24, and DAPI, each conjugated with alexa fluor 488 (green) and 524 (red) (FIGS. 9 and 10). Confocal microscopy facilitated determination of the morphology of the organoids and protein expression. Unenriched organoids (FIG. 10) had a significant population of apoptotic cells within the central domain. The organoid did not undergo hyperplastia for the culture duration and exhibited a bright CD-24 signal in an elliptical pattern. Anti-Lgr5/GPRCR49 expression was faint (FIG. 10*b*), and expression was limited to the lumendomain of the organoid. Localization of anti-Lgr5/GPRCR49 diminished in the significantly low CD24 populations (FIG. 10A-B).

The topography of the unenriched culture exhibited an elliptical planar morphology (FIG. 10D) in contrast to the enriched organoid, which was spherical (FIG. 9D). The central domain expressed CD-24 (green) and anti-Lgr5/GPCR49 (red), localized in the apical membrane (FIG. 9A-B). CD-24 expression was localized along 4 different membranes (FIG. 9A), and expression was lower in intensity compared to the unenriched organoid. Localized anti-Lgr5/GPCR49 were centered in the apical membrane and expressed in 2 membranes (FIG. 9B). Expression of both markers was strictly limited to the central domain, coinciding with Sox9 (CD-24) and Lgr5 genomic trends. (Gracz, A. D. et al., Sox9 expression marks a subset of CD24-expressing small intestine epithelial stem cells that form organoids in vitro. *Am J Physiol-Gastr L* 2010, 298 (5), G590-G600; 14; Sei, Y. et al, A stem cell marker-expressing subset of enteroendocrine cells resides at the crypt base in the small intestine. *Am J Physiol-Gastr L* 2011, 300 (2), G345-G356).

Discussion

The instant disclosure fulfills the need in developing a cost-effective and fluorescent-free cell isolation devices and methods for application such as tissue engineering. Conventional methods in intestinal stem cell isolation rely on hybridized mice models and complex instrumentation, such as FACS. The instant Example describes a microfluidics method that enriches intestinal stem cell populations using alginate coupled with anti-GPCR49/Lgr5. Furthermore, the enriched lgr5 cells have been grown in appropriate culture medium. After adding the cells in medium, CD24 expression coinciding with Lgr5 expression in the organoid central domain was investigated. This Example describes methods and devices that enrich a select target population while retaining viability, expression, and growth morphology.

This Example describes a one-pass microfluidic alginate capture and release model capable of a 24-fold enrichment to a GPCR49/Lgr5 purity of 49%. Using a pacifying agent, BSA, allowed for a decrease in non-specific binding. The phenomena generates a cascading affect in which coagulated cell types containing lgr5 positive cells adhere to the alginate coating; immediate injection of strained cells was performed to facilitate in dispersion. Chemical interactions and stability between alginate, EDC, 4-arm star PEG, Anti-GPCR49/Lgr5 were increased as the reaction pH became more basic.

Although not bound by any theory, increasing the reaction pH de-protenated active sites in the 4-star PEG, which can constrain antibody interactions to the 4 active sites, thus inhibiting covalent binding to the alginate matrix creating an adsorption effect. The probability of the interactions can be reduced by introducing a capping reagent to inhibit unsolicited side reactions. In contrast to conventional methods, the disclosed methods can be used for multiplexing, allowing many devices to be run in parallel and increasing throughput. Furthermore, the disclosed methods allowed for fluorescent-label free isolation of intestinal stem cells while retaining similar growth morphology in situ.

Culture of the injected and isolated cell populations provided information regarding cell composition, morphology, and the effect of soluble factors, specifically Wnt3a. The injected and released samples were cultured in similar fashion as previously reported in literature. To investigate morphological growth of the Lgr5 enriched population and unaltered digestate, cultures were run in parallel to assess differences in proliferation and morphology. The growth within un-enriched population had significant morphological variations between organoid to organoid. Many of the organoids did not undergo hyperplasia and remained in cyst-like state, whereas others formed monolithic fibroplastic layers. Whether Wnt3a was present or absent within the culture, the unenriched organoids remained unaffected and sustained similar morphologies. The unenriched population contain doublets of paneth-lgr5 positive cells, which sustain the necessary Wnt signaling; thus, a null effect was noticed in the presence of the cofactor. In the absence of Wnt3a, it was noted that the plating efficiency amongst the unenriched population was slightly higher than the enriched suspension; this being indicative of paneth cell niche signaling allowing for improved long-term organoid viability. Enriched organoids were plated in similar fashion to the injected suspension, but the significant difference resided in the morphological changes and plating efficiency of the released GPCR49/lgr5 positive cells.

In the absence of Wnt3a, the plating efficiency of the enriched population was within the range of 6% as previously reported. Age progression of the Wnt3a deficient cells exhibited lumen formation and an eventual hyperplasic onset. These fall in line with the previous reported morphology of single Lgr5 derived organoids. Secreted apoptotic cells surrounded the enriched organoid, which indicated a self-sustained nature, mimicking in vivo proliferation. The presence of Wnt3a led to an increase in platting efficiency as well as morphological changes. At similar time points in the Wnt3a deficient cultures, morphology were cyst-like and exhibited a progenitor phenotype. The addition of this constituent facilitates an activation of r-spondin1 and sustains the paneth cell niche without direct contact.

Recent literature suggests that intestinal stem cells potentially reside in two coded genes, Sox9 and Lgr5. These expression trends are bound the intra and extracellular domains of the cells, which can be identified with CD24 and GPCR49 respectively. To investigate the expression trends within the organoids, immuno-histochemical coupled with confocal microscopy gave insight into these patterns. The unenriched organ exhibits a cyst-like morphology harboring apoptotic cells within the central domain. CD24 expression was illustrated in the apical membrane within the central lumen while GPCR49/Lgr5 exhibited positive expression in low expression CD24 regions; this trend is similar to previously discovered genomic expression. Conversely, the enriched organoid exhibited a slightly different morphology but similar immuno-expression patterns. The images indicate a smaller organoid with a small central lumen formed yet to harbor any apoptotic cells. CD24 and GPCR49/Lgr5 expression was bound in the central domain with similar expression patterns as the latter. The presented images eluded to that the microfluidics enrichment process retained similar morphological outcomes as previously reported.

The Example discloses methods and devices that can be used for cell sorting and tissue engineering. The Example describes an intestinal stem cell isolation technique from wild-type intestinal digestate. The current convention is limited to transgenic mice models and complex instrumentation to isolate these cells. The disclosed methods allow the end-user to isolate cell subtypes in a speedy process while retaining cell viability.

Example 3—Multistage Capture and Release Device and Methods

This Example relates to compositions and methods for a multistage, highly specific capture and release of biological materials, such as cells.

The first step in the separation of target cells whose identity is defined by two different surface receptors (e.g. cell populations from whole blood that are both CD31+ and FLK1+). FIG. 11A-D represent a configuration of alginate-hydrogel based devices that include capture stages for each of two antibodies. In some embodiments, more than two antibodies are contemplated.

In FIG. 11A-D, a sample was injected via a syringe pump into the first alginate-based capture stage ("Marker 1 isolation"/FIG. 11A). This stage was connected to stage B, which was a 2-way valve. In its "closed" configuration, this valve allowed the waste from stage A to pass through to a collection tube. After the waste went through, the waste stream was closed using, for example, a pinch valve. (FIG. 11B). The purpose of the calcium chloride was to neutralize the EDTA in the cell suspension emerging from stage (FIG. 11A). To ensure mixing of the calcium chloride solution with this cell suspension, the combined output (which was in laminar flow) was sent into a mixing chamber (FIG. 11C) containing herringbone features. The mixed solution then entered stage (FIG. 11D), where the cells expressing receptors for the second capture molecule were captured. The final step in the separation process was the injection of an EDTA solution into the stage A (FIG. 11A) inlet, which releases the captured cells from stage B (FIG. 11B). This solution was collected in a tube containing an excess of culture medium to minimize any deleterious effect of the EDTA on the cells.

This Example showed the ability of this dual-stage capture system to isolate endothelial progenitor cells (EPCs) from untreated whole blood. The objective was to capture cells that are CD34+/FLK1+. FIG. 12 shows cell counts (obtained by flow cytometry) of the cells emerging from stage A and stage B. In FIG. 12, the various populations shown represent categories of CD34+ cells and the "total" column represents the total number of cells released. The objective of the second capture device was to remove CD34+ cells that do not express the second marker, FLK-1, namely the CD34+ cells that are also CD45+. The sharp decrease in the number of CD45+ cells coming out of the second capture stage relative to the first capture stage shows this enrichment.

Other aspects, modifications, and embodiments are within the scope of the following claims.

The invention claimed is:

1. A hydrogel composition comprising:
a plurality of alginic acid molecules;
divalent cations crosslinking the alginic acid molecules;
a plurality of branched polyethylene glycol molecules comprising a plurality of attachment points; and
one or more binding agents,
wherein the alginic acid molecules are conjugated to the branched polyethylene glycol molecules by a first of the attachment points, and the one or more binding agents are conjugated to the branched polyethylene glycol molecules by a second of the attachment points, and wherein the hydrogel composition dissolves in the presence of a chelator.

2. The composition of claim 1, wherein the branched polyethylene glycol molecules are four-arm molecules.

3. The composition of claim 1, wherein the one or more binding agents is an antibody, antibody fragment, peptidomimetic compound, peptide, small molecule, or a nucleic acid.

4. The composition of claim 3, wherein the antibody is selected from the group consisting of antibodies against GPR49, LGR5, CD24, FLK1, CD45, CD31, CD34, and sca-1 proteins.

5. A method of capturing and releasing target biological materials from a sample, the method comprising:

(a) providing a microfluidic device comprising one or more chambers for receiving fluids, wherein at least one of the one or more chambers comprises a surface coated with a hydrogel composition, the hydrogel composition comprising:
a plurality of alginic acid molecules; divalent cations crosslinking the alginic acid molecules; branched polyethylene glycol molecules comprising a plurality of attachment points; and one or more binding agents that bind to the target biological materials;
wherein the alginic acid molecules are conjugated to the branched polyethylene glycol molecules by a first of the attachment points, and the one or more binding agents are conjugated to the branched polyethylene glycol molecules by a second of the attachment points, and wherein the hydrogel composition dissolves in the presence of a chelator;
(b) introducing the sample comprising target and non-target biological materials into the one or more chambers under conditions effective to bind the target biological materials to the hydrogel composition; and
(c) releasing the target biological materials using a chelator.

6. The method of claim 5, further comprising removing the unbound non-target materials from the sample prior to step (c).

7. A method of making a hydrogel composition, the method comprising:
(a) reacting branched polyethylene glycol molecules comprising a plurality of attachment points with one or more binding agents in a buffer; and
(b) reacting the branched polyethylene glycol binding agent solution with alginic acid molecules and divalent cations to form a functionalized hydrogel, the functionalized hydrogel comprising branched polyethylene glycol molecules conjugated at least one alginic acid molecule by a first of the attachment points and further conjugated to one or more binding agents by a second of the attachment points, wherein the hydrogel composition dissolves in the presence of a chelator.

8. The method of claim 7, wherein the polyethylene glycol molecule is a four-arm molecule.

9. The method of claim 7, wherein the one or more binding agents is an antibody, antibody fragment, peptidomimetic compound, peptide, small molecule, or a nucleic acid.

10. The method of claim 9, wherein the antibody is selected from the group consisting of antibodies against GPR49, LGR5, CD24, FLK1, CD45, CD31, CD34, and sca-1 proteins.

11. The hydrogel composition of claim 1, wherein the divalent cations are $Ca^{2+}$ cations.

12. The method of claim 5, wherein the divalent cations are $Ca^{2+}$ cations.

13. The method of claim 7, wherein the divalent cations are $Ca^{2+}$ cations.

* * * * *